US005759552A

United States Patent [19]
Paoletti et al.

[11] Patent Number: 5,759,552
[45] Date of Patent: Jun. 2, 1998

[54] MAREK'S DISEASE VIRUS RECOMBINANT POXVIRUS VACCINE

[75] Inventors: Enzo Paoletti, Delmar; Jill Taylor, Albany; James Tartaglia, Schenectady, all of N.Y.; Louis Ross, Alconbury, United Kingdom

[73] Assignee: Virogenetics Corporation, Troy, N.Y.

[21] Appl. No.: 207,792

[22] Filed: Mar. 7, 1994

Related U.S. Application Data

[63] Continuation of Ser. No. 1,391, Jan. 4, 1993, abandoned, which is a continuation-in-part of Ser. No. 820,077, Jan. 13, 1992, abandoned, and a continuation-in-part of Ser. No. 105,483, Aug. 12, 1993, Pat. No. 5,494,807, which is a continuation of Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, abandoned.

[51] Int. Cl.$^6$ .................... A61K 39/255; A61K 39/275; A61K 39/295; C12N 7/01
[52] U.S. Cl. .................... 424/199.1; 424/229.1; 435/235.1; 435/320.1; 435/69.1; 435/69.3
[58] Field of Search .................... 435/69.1, 69.3, 435/91, 172.3, 235.1, 240.2, 320.1; 536/23.1, 23.72; 424/199.1, 229.1; 935/12, 32, 41, 57, 63, 65, 70

[56] References Cited

U.S. PATENT DOCUMENTS

| 4,603,112 | 7/1986 | Paoletti et al. | 435/235.1 |
| 5,021,347 | 6/1991 | Yasui et al. | |
| 5,093,258 | 3/1992 | Cohen | 435/235.1 |
| 5,174,993 | 12/1992 | Paoletti | 424/89 |
| 5,180,675 | 1/1993 | Drillien et al. | 435/235.1 |
| 5,364,773 | 11/1994 | Paoletti | 435/69.1 |
| 5,558,860 | 9/1996 | Ross et al. | 424/93.2 |

FOREIGN PATENT DOCUMENTS

| 24458/88 | 5/1989 | Australia. | |
| 261940 | 3/1988 | European Pat. Off. | C12N 15/00 |
| 0284416 | 9/1988 | European Pat. Off. | |
| 0314569 | 3/1989 | European Pat. Off. | |
| 0 520 753 A1 | 12/1992 | European Pat. Off. | C12N 15/38 |
| 89/01973 | 3/1989 | WIPO | C12N 15/00 |
| WO 89/12684 | 12/1989 | WIPO. | |
| 9002803 | 3/1990 | WIPO | C12N 15/38 |

OTHER PUBLICATIONS

Bertholet, C., R. Drillien, and R. Wittek, Proc. Natl. Acad. Sci. USA 82, 2096–2100 (1985).

Boursnell, M.E.G., P.F. Green, A.C.R. Samson, J.I.A. Campbell, A. Deuter, R.W. Peters, N.S. Millar, P.T. Emmerson, and M.M. Binns, Virology 178, 297–300 (1990a).

Boursnell, M.E.G., P.F. Green, J.I.A. Campbell, A. Deuter, R.W. Peters, F.M. Tomley, A.C.R. Samson, P. Chambers, P.T. Emmerson, and M.M. Binns, J. Gen. Virol. 71, 621–628 (1990b).

Calnek, B.W. and R.L. Witter, In Diseases of Poultry 9th Edition, eds. B.W. Calnek, H.J. Barnes, C.W. Beard, W.M. Reid and H.W. Yoder, Jr. (Iowa State University Press, Ames, Iowa, USA) pp. 342–385 (1991).

Calnek, B.W., K.A. Schat, L.J.N. Ross, W.R. Shek, and C.-L.H. Chen, Int. J. Cancer 33, 389–398 (1984).

Calnek, B.W., K.A. Schat, E.D. Heller, and C. Buscaglia, In Proc Int Symp Marek's Dis. ed. B.W. Calnek and J.L. Spencer (Am. Assoc. Avian Pathol, Kennett Square, PA) pp. 173–187 (1985).

Cantin, E.M., R. Eberle, J.L. Baldick, B. Moss, D.E. Willey, A.L. Notkins and H. Openshaw, Proc. Nat. Acad. Sci USA 84, 5908–5912 (1987).

Casadaban, M.J., A. Martinez–Arias, S.K. Shapira, and J. Chow, Methods in Enzymology 100, 293–308 (1983).

Clewell, D.B., and D.R. Helinski, Proc. Natl. Acad. Sci. USA 62, 1159–1166 (1969).

Clewell, D.B., J. Bacteriol. 110, 667–676 (1972).

Colinas, R.J., R.C. Condit, and E. Paoletti, Virus Research 18, 49–70 (1990).

Cremer, K.J., M. Mackett, C. Wohlenberg, A.L. Notkins and B. Moss, Science 228, 737–740 (1985).

Edbauer, C., R. Weinberg, J. Taylor, A. Rey–Senelonge, J.F. Bouquet, P. Desmettre, and E. Paoletti, Virology 179, 901–904 (1990).

Engelke, D.R., P.A. Hoener, and F.S. Collins, Proc. Natl. Acad. Sci. USA 85, 544–548 (1988).

Esposito, J.J., Fifth Report of the International Committee on Taxonomy of Viruses, Archives of Virology Supplement 2, eds. R.I.B. Francki, C.M. Faquet, D.L. Knudson, F. Brown, (Springer–Verlag, New York) pp. 91–102 (1991).

Goebel, S.J., G.P. Johnson, M.E. Perkus, S.W. Davis, J.P. Winslow, and E. Paoletti, Virology 179, 247–266 (1990a).

Goebel, S.J., G.P. Johnson, M.E. Perkus, S.W. Davis, J.P. Winslow, and E. Paoletti, Virology 179, 517–563 (1990b).

Guo, P., S. Goebel, M.E. Perkus, J. Taylor, E. Norton, G. Allen, B. Languet, P. Desmettre, and E. Paoletti, J. Virol. 64, 2399–2406 (1990).

Guo, P., S. Goebel, S. Davis, M.E. Perkus, B. Languet, P. Desmettre, G. Allen, and E. Paoletti, J. Virol. 63, 4189–4198 (1989).

Kato, S. and K. Hirai, Adv. Virus Res. 30, 225–277 (1985).

Mandecki, W., Proc. Natl. Acad. Sci. USA 83, 7177–7181 (1986).

Maniatis, T., E.F. Fritsch, and J. Sambrook, Molecular Cloning, Cold Spring Harbor Laboratory, NY 545 pages (1982).

(List continued on next page.)

*Primary Examiner*—Mary E. Mosher
*Attorney, Agent, or Firm*—Frommer Lawrence & Haug LLP; William S. Frommer; Thomas J. Kowalski

[57] ABSTRACT

What is described is a recombinant poxvirus, such as vaccinia virus or fowlpox virus, containing foreign DNA from Marek's disease virus. What is also described is a vaccine containing the recombinant poxvirus for inducing an immunological response in a host animal inoculated with the vaccine.

14 Claims, 7 Drawing Sheets

OTHER PUBLICATIONS

Maniatis, T., E.F. Fritsch, and J. Sambrook, Molecular Cloning, Cold Spring Harbor Laboratory, NY 545 pages (1986).

Marcholi, C.C., R.J. Yancey, E.A. Petrovskis, J.G. Timmins and L.E. Post, J. Virol. 61, 3977–3981 (1987).

Nazerian, K., E.A. Stephens, J.M. Sharma, L.F. Lee, M. Gailitis and R.L. Witter, Avian Diseases 21, 69–76 (1977).

Okazaki, W., H.G. Purchase, B.R. Burmester, Avian Dis 14, 413–429 (1970).

Ono, K., M. Takashima, T. Ishikawa, M. Hayashi, I. Yoshida, T. Knobbe, K. Ikuta, K. Nakajima, S. Ueda, S. Kato and K. Hirai, Avian Dis 29, 533–539 (1985).

Panicali, D., and E. Paoletti, Proc. Natl. Acad. Sci. USA 79, 4927–4931 (1982).

Paoletti, E., B.L. Lipinskas, C. Samsonoff, S. Mercer and D. Panicali, Proc. Nat. Acad. Sci. 81, 193–197 (1984).

Payne, L.N., J.A. Frazier, P.C. Powell, Int. Rev. Exp. Pathol. 16, 59–153 (1976).

Payne, L.N. In Marek's Disease, ed. L.N. Payne (Martinus Nijhoff, Boston) pp. 43–76 (1985).

Perkus, M.E., S.J. Goebel, S.W. Davis, G.P. Johnson, K. Limbach, E.K. Norton, and E. Paoletti, Virology 179, 276–286 (1990).

Perkus, M.E., K. Limbach, and E. Paoletti, J. Virol. 63, 3829–3836 (1989).

Perkus, M.E., A. Piccini, B.R. Lipinskas, and E. Paoletti, Science 229, 981–984 (1985).

Piccini, A., M.E. Perkus, and E. Paoletti, In Methods in Enzymology, vol. 156, eds. Wu, R., and Grossman, L., (Academic Press) pp. 545–563 (1987).

Schat, K.A., Cancer Surveys 6, 1–37 (1987).

Shapira, S.K., J. Chou, F.V. Richaud, and M.J. Casadaban, Gene 25, 71–82 (1983).

Tabor, S., and C.C. Richardson, Proc. Natl. Acad. Sci. USA 84, 4767–4771 (1987).

Tartaglia, J., S. Pincus and E. Paoletti, Crit. Revs. in Immunol. 10, 13–30 (1990).

Taylor, J., S. Pincus, J. Tartaglia, C. Richardson, G. Alkhatib, D. Briedis, M. Appel, E. Norton, and E. Paoletti, J. Virol. 65, 4263–4272 (1991).

Yuen, L., and B. Moss, Proc. Natl. Acad. Sci. USA 84, 6417–6421 (1987).

Taylor et al J. Virol. vol. 64 pp. 1441–1450 (1990).

Taylor et al Vaccine vol. 6 pp. 497–503 (1988).

Taylor et al Vaccine vol. 6 pp. 504–508 (1988).

Ross et al J. Gen Virol vol. 72 pp. 949–954 (1991).

Piccini et al Methods in Enzymology vol. 153 pp. 545–563 (1987).

Lewin, R., Science 237 (Sep. 25, 1987).

Reeck et al., Cell 50:667 (Aug. 28, 1987).

Churchill et al., Nature 221:744–747 (1969).

Schat et al., J. Natl. Cancer Inst. 60(5):1075–1081 (1978).

Blacklaws et al., Virology 177:727–736 (1990).

Boyle et al., Virus Research 10:343–356 (1988).

Ogawa et al., Vaccine 8:486–490 (1990).

Okazaki et al., "Protection Against Marek's Disease by Vaccination with a Herpesvirus of Turkeys", pp. 413–429 (1970).

Rispens et al., "Control of Marek's Disease in the Netherlands . . . Laboratory Vaccination Trials", pp. 108–125.

Witter et al., Avian Pathology 8:145–156 (1979).

Yuen et al., Proc. Natl. Acad. Sci. USA 84:6417–6421 (1987).

Sanger et al., Proc. Natl. Acad. Sci. USA 74(12):5463–5467 (1977).

Tsurushita et al., Gene 62:135–139 (1988).

Shirakawa et al., Gene 28:127–132 (1984).

Silva et al., Virology 136:307–320 (1984).

Ross et al., J. Gen. Virol. 70:1789–1804 (1989).

Yanagida et al., Journal of Virology 66(3):1402–1408 (1992).

Nazerian et al., Journal of Virology 66(3:1409–1413 (1992).

Ross et al., J. Gen. Virol. 72(4):939–947 (1991).

Ross et al., Proceedings XIX World's Poultry Congress, Amsterdam, The Netherlands 1:144–149 (1992).

Davison et al., J. Mol. Biol. 210:771–784 (1980).

Davison et al., J. Mol. Biol. 210:749–769 (1980).

Meulemans, G. et al. 1988, Avian Pathology, vol. 17, pp. 821–827.

Chambers, T.M. et al. 1988. Virology, vol. 167, pp. 414–421.

Joklik, W. K. et al. 17 edition, Zinsser Microbiology, p. 973, Appleton–Centurion–Crofts, New York, 1980.

Andrewes, C. et al. Viruses of Vertebrates, pp. 373–375. Bailliere Tindall, London, 1978.

Earl, P.L. et al. Journal of Virology, vol. 64, pp. 2448–2451, 1990.

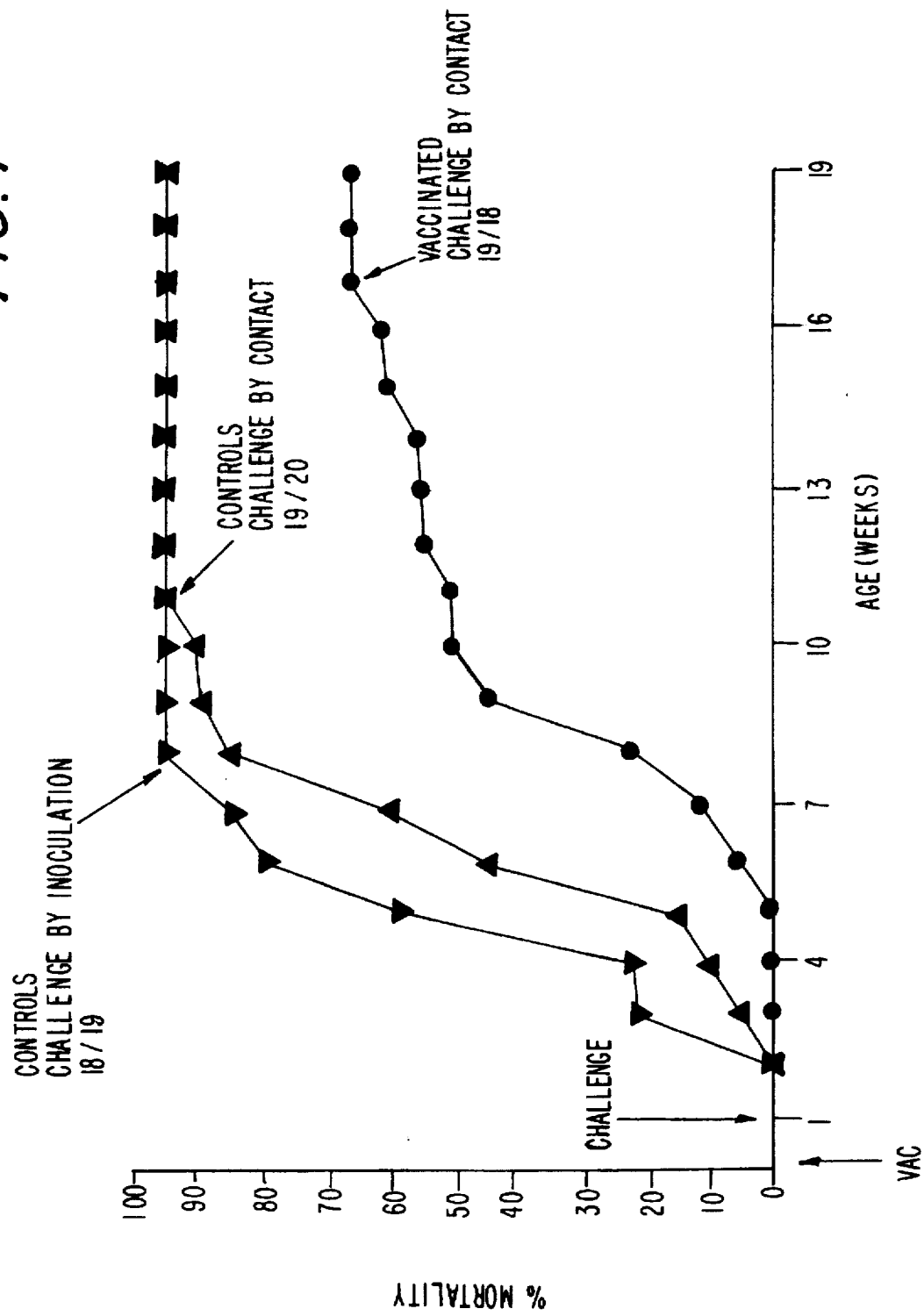

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

TAATTAACTA GCTACCCGGG    20

( 2 ) INFORMATION FOR SEQ ID NO:2:

( i ) SEQUENCE CHARACTERISTICS:

( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATTCCCGGG TAGCTAGTTA ATTACATG                                                        2 8

( 2 ) INFORMATION FOR SEQ ID NO:3:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGCTTCCCGG GTAAGTAATA CGTCAAGGAG AAAACGAAAC GATCTGTAGT TAGCGGCCGC        6 0

CTAATTAACT AAT                                                                                   7 3

( 2 ) INFORMATION FOR SEQ ID NO:4:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATTAGTTAAT TAGGCGGCCG CTAACTACAG ATCGTTTCGT TTTCTCCTTG ACGTATTACT        6 0

TACCCGGGA                                                                                          6 9

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTAGTTAATT AGGCGGCCGC                                                                     2 0

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGATTACTAT GAAGGATCCG TT                                                                2 2

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AACGGATCCT TCATAGTAAT                                                                      2 0

( 2 ) INFORMATION FOR SEQ ID NO:8:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:8:

CGATTACTAG ATCTGAGCTC CCCGGGCTCG AGGGATCCGT T     41

( 2 ) INFORMATION FOR SEQ ID NO:9:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:9:

AACGGATCCC TCGAGCCCGG GGAGCTCAGA TCTAGTAAT     39

( 2 ) INFORMATION FOR SEQ ID NO:10:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:10:

GATCCGAATT CTAGCT     16

( 2 ) INFORMATION FOR SEQ ID NO:11:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:11:

AGCTAGAATT CG     12

( 2 ) INFORMATION FOR SEQ ID NO:12:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( x i ) SEQUENCE DESCRIPTION: SEQ ID NO:12:

TATGAGTAAC TTAACTCTTT TGTTAATTAA AAGTATATTC AAAAAATAAG TTATATAAAT     60

AGATCTGAAT TCGTT     75

( 2 ) INFORMATION FOR SEQ ID NO:13:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( x i ) SEQUENCE DESCRIPTION: SEQ ID NO:13:

AACGAATTCA GATCTATTTA TATAACTTAT TTTTTGAATA TACTTTTAAT TAACAAAAGA     60

GTTAAGTTAC TCA     73

( 2 ) INFORMATION FOR SEQ ID NO:14:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAAATGGGCG TGGATTGTTA ACTTATATA ACTTATTTTT TGAATATAC                  49
```

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ACACGAATGA TTTTCTAAAG TATTTGGAAA GTTTATAGG TAGTTGATAG AACAAAATAC       60

ATAATTT                                                               67
```

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TCTATCAACT ACCTATAAAA CTTTCCAAAT ACTTTAGAAA ATCATTCGTG T               51
```

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
TGTAAAAATA AATCACTTTT TATACTAAGA TCTCCCGGGC TGCAGC                    46
```

( 2 ) INFORMATION FOR SEQ ID NO:18:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GGCCGCTGCA GCCCGGGAGA TCTTAGTATA AAAAGTGATT TATTTTTACA AAATTATGTA     60

TTTTGT                                                                66
```

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
TTTCTGTATA TTTGCACCAA TTTAGATCTT ACTCAAAATA TGTAACAATA                    50
```

( 2 ) INFORMATION FOR SEQ ID NO:20:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
TGTCATTTAA CACTATACTC ATATTAATAA AAATAATATT TATT                          44
```

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GATCCTGAGT ACTTTGTAAT ATAATGATAT ATATTTCAC TTTATCTCAT TTGAGAATAA          60

AAAGATCTTA GG                                                             72
```

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AATTCCTAAG ATCTTTTTAT TCTCAAATGA GATAAAGTGA AAATATATAT CATTATATTA         60

CAAAGTACTC AG                                                             72
```

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GATCCAGATC TCCCGGGAAA AAAATTATTT AACTTTTCAT TAATAGGGAT TGACGTATG          60

TAGCGTACTA GG                                                             72
```

( 2 ) INFORMATION FOR SEQ ID NO:24:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
AATTCCTAGT ACGCATCATA CGTCAAATCC CTATTAATGA AAGTTAAAT AATTTTTTC           60

CCGGGAGATC TG                                                             72
```

( 2 ) INFORMATION FOR SEQ ID NO:25:

( i ) SEQUENCE CHARACTERISTICS:
        ( A ) LENGTH: 3660 base pairs ( B ) TYPE: nucleic acid
( C ) STRANDEDNESS: single
( D ) TOPOLOGY: linear ( x i ) SEQUENCE DESCRIPTION: SEQ ID NO:25:

| | | | | | |
|---|---|---|---|---|---|
| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAAGAAGTAC | CAGTAAAAAG | 120 |
| TGTGGCATAT | GCATAGAAGA | AATAAACAAA | AAACATATTT | CCGAACAGTA | TTTTGGAATT | 180 |
| CTCCCAAGTT | GTAAACATAT | TTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAA | TATTATATAA | TAGATATAAG | 360 |
| AAAATGATTT | TTACAAAAAT | AACCTATAAG | AACAATAAAA | ATATAATTAC | ATTTACGGAA | 420 |
| AATAGCTGGT | TTTAGTTTAC | CAACTTAGAG | TAATTATCAT | ATTGAATCTA | TATTGTTTTT | 480 |
| TAGTTATATA | AAAACATGAT | TAGCCCCCAA | TCGGATGAAA | ATATAAAGA | TGTTGAGAAT | 540 |
| TTCGAATACA | ACAAAAGAG | GAATCGTACG | TTGTCCATAT | CCAAACATAT | AATAAAAAT | 600 |
| TCAAAAGTAG | TATTATACTG | GATGTTTAGA | GATCAACGTG | TACAAGATAA | TTGGGCTTTA | 660 |
| ATTACGCAC | AACGATTAGC | GTTAAAACTC | AAAATACCTC | TAAGAATATG | CTTTGTGTC | 720 |
| GTGCCAAAAT | TTCACACTAC | TACTTCTAGA | CACTTTATGT | TTTAATATC | CGGTCTTAAA | 780 |
| GAAGTCGCGG | AAGAATGTAA | AAGACTATGT | ATAGGGTTTT | CATTGATATA | TGGCGTACCA | 840 |
| AAAGTAATAA | TTCCGTGTAT | AGTAAAAAA | TACAGAGTCG | GAGTAATCAT | AACGGATTTC | 900 |
| TTTCCATTAC | GTGTTCCCGA | AAGATTAATG | AAACAGACTG | TAATATCTCT | TCCAGATAAC | 960 |
| ATACCTTTTA | TACAAGTAGA | CGCTCATAAT | ATAGTACCTT | GTTGGGAAGC | TTCTGATAAA | 1020 |
| GAAGAATACG | GTGCACGAAC | TTTAAGAAAA | AAGATATTTG | ATAAATTATA | TGAATATATG | 1080 |
| ACAGAATTTC | CTGTTGTTCG | TAAACATCCA | TACGGTCCAT | TTCTATATC | TATTGCAAAA | 1140 |
| CCCAAAAATA | TATCATTAGA | CAAGACGGTA | TTACCCGTAA | AATGGGCAAC | GCCTGGAACA | 1200 |
| AAAGCTGGAA | TAATTGTTTT | AAAAGAATTT | ATAAAAACA | GATTACCGTC | ATACGACGCG | 1260 |
| GATCATAACA | ATCCTACGTG | TGACGCTTTG | AGTAACTTAT | CTCCGTGGCT | ACATTTTGGT | 1320 |
| CATGTATCCG | CACAACGTGT | TGCCTTAGAA | GTATTAAAAT | GTATACGAGA | AAGCAAAAAA | 1380 |
| AACGTTGAAA | CGTTTATAGA | TGAAATAATT | GTAAGAAGAG | AACTATCGGA | TAATTTTTGT | 1440 |
| TACTATAACA | AACATTATGA | TAGTATCCAG | TCTACTCATT | CATGGGTTAG | AAAAACATTA | 1500 |
| GAAGATCACA | TTAATGATCC | TAGAAAGTAT | ATATATTCCA | TTAAACAACT | CGAAAAAGCG | 1560 |
| GAAACTCATG | ATCCTCTATG | GAACGCGTCA | CAAATGCAGA | TGGTGAGAGA | AGGAAAAATG | 1620 |
| CATAGTTTTT | TACGAATGTA | TTGGGCTAAG | AAGATACTTG | AATGGACTAG | AACACCTGAA | 1680 |
| GACGCTTTGA | GTTATAGTAT | CTATTTGAAC | AACAAGTACG | AACTAGACGG | CACGGATCCT | 1740 |
| AACGGATACG | TAGGTTGTAT | GTGGTCTATT | TGCGGATTAC | ACGATAGAGC | GTGGAAAGCA | 1800 |
| AGACCGATAT | TTGGAAAGAT | AAGATATATG | AATTATGAGA | GTTCTAAGAA | GAAATTTGAT | 1860 |
| GTTGCTGTAT | TTATACAGAA | ATACAATTAA | GATAAATAAT | ATACAGCATT | GTAACCATCG | 1920 |
| TCATCCGTTA | TACGGGGAAT | AATATTACCA | TACAGTATTA | TTAAATTTTC | TTACGAAGAA | 1980 |
| TATAGATCGG | TATTTATCGT | TAGTTTATTT | TACATTTATT | AATTAAACAT | GTCTACTATT | 2040 |
| ACCTGTTATG | GAAATGACAA | ATTTAGTTAT | ATAATTTATG | ATAAAATTAA | GATAATAATA | 2100 |
| ATGAAATCAA | ATAATTATGT | AAATGCTACT | AGATTATGTG | AATTACGAGG | AAGAAAGTTT | 2160 |
| ACGAACTGGA | AAAAATTAAG | TGAATCTAAA | ATATTAGTCG | ATAATGTAAA | AAAAATAAAT | 2220 |

```
GATAAAACTA ACCAGTTAAA AACGGATATG ATTATATACG TTAAGGATAT TGATCATAAA      2280

GGAAGAGATA CTTGCGGTTA CTATGTACAC CAAGATCTGG TATCTTCTAT ATCAAATTGG      2340

ATATCTCCGT TATTCGCCGT TAAGGTAAAT AAAATTATTA ACTATTATAT ATGTAATGAA      2400

TATGATATAC GACTTAGCGA AATGGAATCT GATATGACAG AAGTAATAGA TGTAGTTGAT      2460

AAATTAGTAG GAGGATACAA TGATGAAATA GCAGAAATAA TATATTTGTT TAATAAATTT      2520

ATAGAAAAAT ATATTGCTAA CATATCGTTA TCAACTGAAT TATCTAGTAT ATTAAATAAT      2580

TTTATAAATT TTATAAATTT TAATAAAAAA TACAATAACG ACATAAAGAT ATTTAATCTT      2640

TAATTCTTGA TCTGAAAAAC ACATCTATAA AACTAGATAA AAAGTTATTC GATAAAGATA      2700

ATAATGAATC GAACGATGAA AAATTGGAAA CAGAAGTTGA TAAGCTAATT TTTTTCATCT      2760

AAATAGTATT ATTTTATTGA AGTACGAAGT TTTACGTTAG ATAAATAATA AAGGTCGATT      2820

TTTACTTTGT TAAATATCAA ATATGTCATT ATCTGATAAA GATACAAAAA CACACGGTGA      2880

TTATCAACCA TCTAACGAAC AGATATTACA AAAAATACGT CGGACTATGG AAAACGAAGC      2940

TGATAGCCTC AATAGAAGAA GCATTAAAGA AATTGTTGTA GATGTTATGA AGAATTGGGA      3000

TCATCCTCAA CGAAGAAATA GATAAAGTTC TAAACTGGAA AAATGATACA TTAAACGATT      3060

TAGATCATCT AAATACAGAT GATAATATTA AGGAAATCAT ACAATGTCTG ATTAGAGAAT      3120

TTGCGTTTAA AAAGATCAAT TCTATTATGT ATAGTTATGC TATGGTAAAA CTCAATTCAG      3180

ATAACGAACA TTGAAAGATA AAATTAAGGA TTATTTTATA GAAACTATTC TTAAAGACAA      3240

ACGTGGTTAT AAACAAAAGC CATTACCCGG ATTGGAAACT AAAATACTAG ATAGTATTAT      3300

AAGATTTTAA AAACATAAAA TTAATAGGTT TTTATAGATT GACTTATTAT ATACAATATG      3360

GATAAAGAT ATATATCAAC TAGAAAGTTG AATGACGGAT TCTTAATTTT ATATTATGAT      3420

TCAATAGAAA TTATTGTCAT GTCGTGTAAT CATTTTATAA ATATATCAGC GTTACTAGCT      3480

AAGAAAAACA AGGACTTTAA TGAATGGCTA AAGATAGAAT CATTTAGAGA AATAATAGAT      3540

ACTTTAGATA AAATTAATTA CGATCTAGGA CAACGATATT GTGAAGAACT TACGGCGCAT      3600

CACATTCCAG TGTAATTATT GAGGTCAAAG CTAGTAACTT AATAGATGAC AGGACAGCTG      3660
```

( 2 ) INFORMATION FOR SEQ ID NO:26:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
CTAGACACTT TATGTTTTTT AATATCCGGT CTTAAAAGCT TCCCGGGGAT CCTTATACGG      60

GGAATAAT                                                                68
```

( 2 ) INFORMATION FOR SEQ ID NO:27:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
ATTATTCCCC GTATAAGGAT CCCCCGGGAA GCTTTTAAGA CCGGATATTA AAAACATAA       60

AGTGT                                                                   65
```

( 2 ) INFORMATION FOR SEQ ID NO:28:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

```
GATCAGAAAA ACTAGCTAGC TAGTACGTAG TTAACGTCGA CCTGCAGAAG CTTCTAGCTA        60

GCTAGTTTTT AT                                                           72
```

( 2 ) INFORMATION FOR SEQ ID NO:29:

( i ) SEQUENCE CHARACTERISTICS:
    ( A ) LENGTH: 73 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

```
AGCTATAAAA ACTAGCTAGC TAGAAGCTTC TGCAGGCTCG ACGTTAACTA CGTACTAGCT        60

AGCTAGTTTT TCT                                                          73
```

( 2 ) INFORMATION FOR SEQ ID NO:30:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

```
GACCTCGTCG ACAATACGAC TCACTATAGG GAG                                    33
```

( 2 ) INFORMATION FOR SEQ ID NO:31:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

```
GAAGAATATG CAATTCCGCC TAAAATAGTG CATTACGATA CAAACTTAA                   49
```

( 2 ) INFORMATION FOR SEQ ID NO:32:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

```
ATGCACTATT TTAGGCGGAA TTGCATATTC TTCCTTATAG TTATTC                      46
```

( 2 ) INFORMATION FOR SEQ ID NO:33:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

```
ATATCTACGA TGATTTCTA GGTTCGGGAC ATTTTC                                  36
```

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GTCCCGAACC TAGAAAATCA TCGTAGATAT TTTCTG        36

( 2 ) INFORMATION FOR SEQ ID NO:35:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CCTCAGGAAT TCGTCGACTA TTTACACAGC ATCATCTTCT GAG        43

( 2 ) INFORMATION FOR SEQ ID NO:36:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TGAGATATAT CTAAAGAAGA ATACTTTCAT TACGATACAA ACTTAAC        47

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

TAATATAATC TTTTATAC        18

( 2 ) INFORMATION FOR SEQ ID NO:38:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

CCGTTCAGCT TCTTCGTCAA TGGTACAACA CGGCTGTTAG AC        42

( 2 ) INFORMATION FOR SEQ ID NO:39:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GAGCGGTCGA CAAGCTTATA GGCGGGAATA TGC        33

( 2 ) INFORMATION FOR SEQ ID NO:40:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

```
TGTTGTACCA TTGACGAAGA AGCTGAACGG TTTGCATAGT TTGTTATC                    48
```

( 2 ) INFORMATION FOR SEQ ID NO:41:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

```
ATGAAAGTAT TCTTCTTTAG ATATATCTCA TCCAC                                  35
```

( 2 ) INFORMATION FOR SEQ ID NO:42:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
AATTAACCCG GGATCCAAGC TTCTAGCTAG CTAATTTTTA TAGCGGCCGC TATAATCGTT       60

AACTTATTAG                                                              70
```

( 2 ) INFORMATION FOR SEQ ID NO:43:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

```
CTAGCTAGAA GCTTGGATCC CGGGTTAATT AATTAATAAA AAGCGGCCGC GTTAAAGTAG       60

AAAAATG                                                                 67
```

( 2 ) INFORMATION FOR SEQ ID NO:44:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
GTTACATATG TACAGAATCT GATCATAG                                          28
```

( 2 ) INFORMATION FOR SEQ ID NO:45:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
GCTAGAATTC TCTTAGTTTT TATAGTTG                                          28
```

MAREK'S DISEASE VIRUS RECOMBINANT POXVIRUS VACCINE

CROSS REFERENCE TO RELATED APPLICATION

This application is a continuation of application Ser. No. 08/001,341, filed Jan. 4, 1993, now abandoned which is a continuation-in-part of U.S. application Ser. No. 07/820, 077, filed Jan. 13, 1992 now abandoned incorporated herein by reference.

This application is also a continuation-in-part of application Ser. No. 105,483, filed Aug. 12, 1993, now U.S. Pat. No. 5,494,807, which is a continuation of U.S. application Ser. No. 847,951, filed Mar. 6, 1992, now abandoned, which in turn is a continuation-in-part of application Ser. No. 713, 967, filed Jun. 11, 1991, now abandoned, which in turn is a continuation-in-part of application Ser. No. 666,056, filed Mar. 7, 1991, now abandoned.

FIELD OF THE INVENTION

The present invention relates to a modified poxvirus and to methods of making and using the same. More in particular, the invention relates to recombinant poxvirus, which, virus expresses gene products of a Marek's disease virus (MDV) gene, and to vaccines which provide protective immunity against MDV infections.

Several publications are referenced in this application. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

An attenuated vector has been developed by the sequential deletion of six non-essential regions from the Copenhagen strain of vaccinia virus. These regions are known to encode proteins that may have a role in viral virulence. The regions deleted are the tk gene, the hemorrhagic gene, the A-type inclusion gene, the hemagglutinin gene and the gene encoding the large subunit of the ribonucleotide reductase as well as the C7L through K1L sequences defined previously (Perkus et. al., 1990). The sequences and genomic locations of these genes in the Copenhagen strain of vaccinia virus have been defined previously (Goebel et al., 1990a,b). The resulting attenuated vaccinia strain is designated as NYVAC.

The technology of generating vaccinia virus recombinants has recently been extended to other members of the poxvirus family which have a more restricted host range.

Fowlpox virus (FPV) has advantageously been engineered as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or heterologous virulent influenza virus challenge (Taylor et al., 1988a). In addition, the surface glycoproteins (fusion and hemagglutinin) of a virulent strain of Newcastle Disease Virus have been expressed in an FPV vector and shown to induce a protective immune response (Taylor et al., 1990; Edbauer et al., 1990, Boursnell et al., 1990a,b).

FPV is the prototypic virus of the Avipox genus of the Poxvirus family. The virus causes an economically important disease of poultry which has been well controlled since the 1920's by the use of live attenuated vaccines. Replication of the avipox viruses is limited to avian species (Esposito, 1991) and there are no reports in the literature of the virus causing a productive infection in any non-avian species including man. This host restriction provides an inherent safety barrier to transmission of the virus to other species and makes use of FPV as a vaccine vector in poultry an attractive proposition.

Marek's Disease is a lymphoproliferative disease of chickens caused by infection with the herpes virus MDV. The disease is characterized by a mononuclear infiltration of one or more of the following areas; peripheral nerves, gonad, iris,, various viscera, muscles and skin (Calnek and Witter, 1991). There are three serotypes of relevance; (1) Serotype 1 which contains oncogenic MDVs (2) Serotype 2 which contains non-oncogenic MDVs and (3) Serotype 3 which contains the closely related herpes virus of turkeys (HVT).

The biology of MDV has been reviewed by Schat (1987). The mode of infection of MDV is via direct or indirect contact between birds, allowing virus spread by the airborne route. After initial contact, three phases of viral infection are apparent. The first phase is defined as an early cytolytic infection. During this phase, productive infection resulting in the release of cell-free virus will occur in the feather follicle epithelium (FFE). At the same time, a nonproductive replication occurs in the lymphoid organs. Defined as a productive-restrictive infection, during this stage, DNA replication occurs and MDV antigens are expressed but the virions produced are non-enveloped and thus non-infectious (Calnek and Witter, 1991). The productive restrictive infection results in the necrosis of B-lymphocytes accompanied by infiltration of macrophages and granulocytes and hyperplasia of reticular cells leading to splenic enlargement (Payne et al., 1976). As a result T cells become activated and express MHC class II (Ia) antigens (Schat, 1987). Activated T cells, but not resting T cells, then become susceptible to infection with MDV (Calnek et al., 1984, 1985). The transient immunosuppression which is associated with early cytolytic infection is probably due, therefore, to lytic infection of B cells in the spleen and bursa (Schat, 1987).

Following this phase, infected birds enter the second stage defined as latent infection. The infected T cells, in which the viral genome is present, do not produce viral antigens nor viral particles. Latent infections are established approximately six days after initial infection of the bird.

The third and final phase is characterized by a secondary cytolytic infection, immunosuppression and tumor formation. This type of infection occurs only with virulent serotype 1 viruses. A secondary cytolytic infection occurs in the FFE and this is the only area where infectious cell-free virus is produced. The importance of this inflammatory infection in tumor formation is not clear, however it is thought that latently infected lymphocytes are attracted to the FFE where they undergo blastogenesis. This may be a requirement for their transformation into tumor cells. In addition, uninfected lymphocytes are attracted to the sites of infection where they become cytolytically infected or transform to tumor cells (Schat, 1987). Permanent immunosuppression is often evident at this time. The change from a latent infection is also characterized by tumor formation in visceral organs, nerves, muscles and skin (Payne et al., 1976, Payne, 1985) and the tumor cells now express a number of MDV antigens.

Prior to the use of vaccines, MDV constituted an economically important disease to the poultry industry. Current vaccines are of three types (1) highly attenuated serotype 1 viruses, (2) naturally avirulent serotype 2 viruses, or (3) the serologically related HVT viruses. The most effective and most extensively used are the HVT vaccines developed by Okazaki et al. (1970). Problems do exist in current vaccination strategies caused by improper handling of the vaccine, interference by maternal antibody and associated stress and concurrent infections. In addition, the emergence of highly virulent MDV strains against which immunization with HVT alone is not protective has led to the inclusion of multiple serotypes in vaccines (reviewed by Calnek and Witter, 1991).

The MDV isolates have been classified as gamma herpes viruses on the basis of their predilection for lymphocytes. However, in recent years, considerable effort has been spent on understanding the genomic organization of MDV and it is now apparent that there is more genetic homology with alpha herpes viruses than with gamma herpes viruses (Ross et al., 1989, 1991). Using this approach, a number of antigens important in eliciting an immune response have been identified. Among these antigens are the HSV1 gB homolog and HSV gD homolog. The HSV1 gB hoomolog was identified by Ross et al. (1989). In other herpes virus diseases the gB glycoprotein has been shown to induce both humoral and cell-mediated immune responses and to confer protective immunity (Cantin et al., 1987, Marchioli et al., 1987, Guo et al., 1990). In MDV infected cells the B antigen is a complex of glycoproteins with molecular weights of 100 kD, 60 kD and 49 kD (Calnek and Witter, 1991). The antigen is located on the infected cell surface and in the cytoplasm (Kato and Hirai, 1985) and is thought to induce neutralizing antibodies (Ono et al., 1985). Similarly, the MDV homolog of the HSV-1 gD was identified by Ross and Binns (1991) and Ross et al. (1991). The HSV gD has been shown to be an effective immunogen against: HSV infection (Paoletti et al., 1984, Cremer et al., 1985).

Although current vaccination strategies against MDV have been quite successful, the emergence of highly virulent MDV strains which are not adequately controlled by current HVT vaccines indicates that inclusion of multiple immunogens of highly virulent strains in a vaccine may provide for a broader immune response.

It can thus be appreciated that provision of a MDV recombinant poxvirus, and of a recombinant based vaccine which provides protective immunity against MDV infections and in which multiple immunogens of MDV could be expressed, would be a highly desirable advance over the current state of technology.

OBJECTS OF THE INVENTION

It is therefore an object of this invention to provide recombinant poxviruses, which viruses express gene products of MDV, and to provide a method of making such recombinant poxviruses.

It is an additional object of this inventLon to provide for the cloning and expression of MDV coding sequences, particularly sequences coding for antigenically relevant glycoproteins from MDV, in a poxvirus vector, particularly vaccinia virus or fowlpox virus vectors.

It is another object of this invention to provide a vaccine which is capable of eliciting MDV neutralizing antibodies and protective immunity against MDV infection.

These and other objects and advantages of the present invention will become more readily apparent after consideration of the following.

STATEMENT OF THE INVENTION

In one aspect, the present invention relates to a recombinant poxvirus containing therein a DNA sequence from MDV in a nonessential region of the poxvirus genome. The poxvirus is advantageously a vaccinia virus or an avipox virus, such as fowlpox virus.

According to the present invention, the recombinant poxvirus expresses gene products of the foreign MDV gene. In particular, the foreign DNA codes for a structural protein, especially an antigenically relevant glycoprotein, from MDV. Advantageously, a plurality of MDV glycoproteins are co-expressed in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from MDV. Advantageously, the DNA codes for and expresses a MDV structural protein, particularly a MDV glycoprotein. A plurality of MDV glycoproteins advantageously are co-expressed in the host. The poxvirus used in the vaccine according to the present invention is advantageously a vaccinia virus or an avipox virus, such as fowlpox virus.

BRIEF DESCRIPTION OF THE DRAWINGS

A better understanding of the present invention will be had by referring to the accompanying drawings, in which:

FIG. 7 is a plot of mortality of chickens over time for control groups (challenged by inoculation or by contact) and a vaccinated group (vaccinated with vFP108 and challenged by contact).

DETAILED DESCRIPTION OF THE INVENTION

Figure 1:
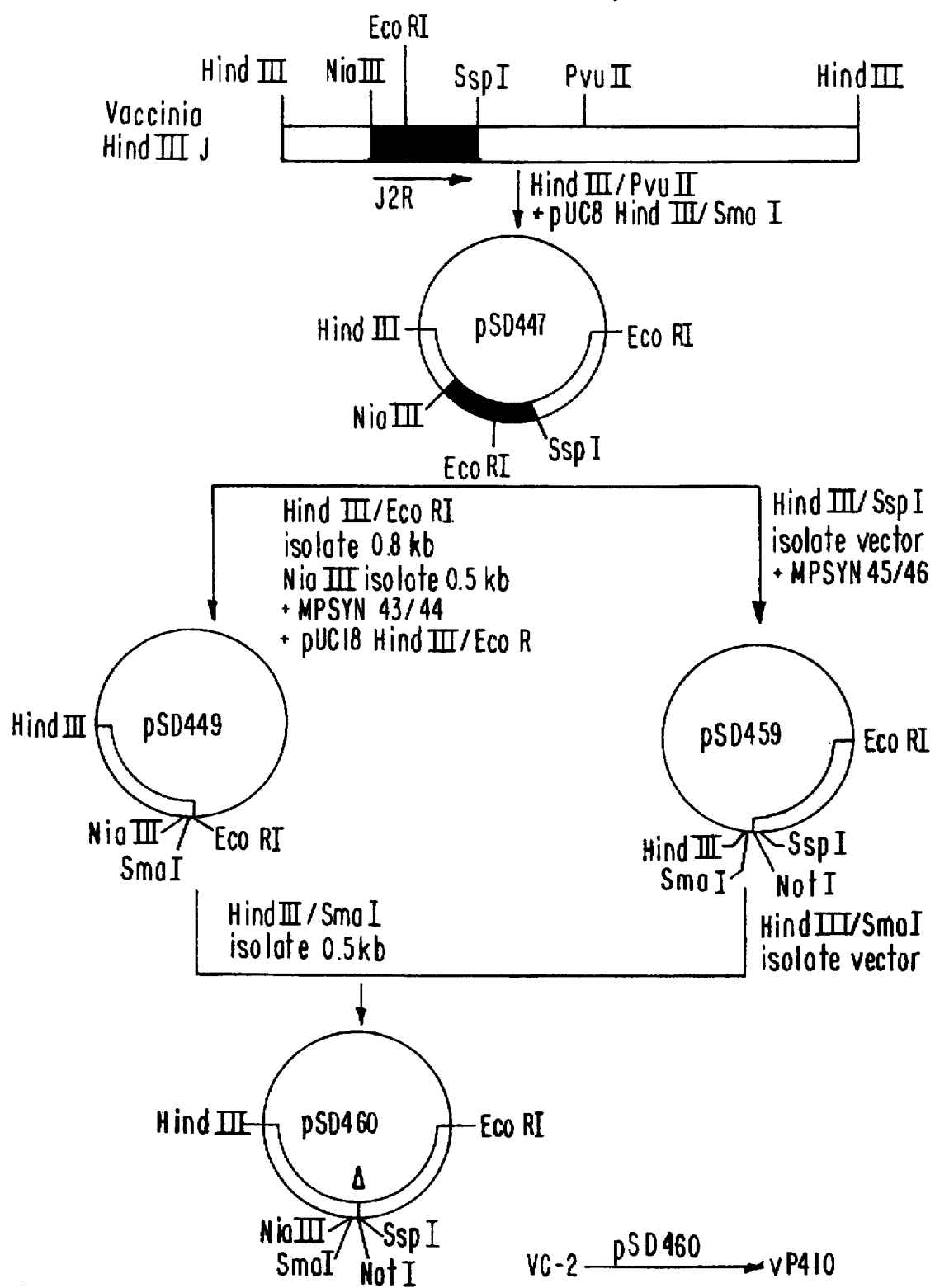
FIG. 1 schematically shows a method for the construction of plasmid pSD460 for deletion of thymidine kinase gene and generation of recombinant vaccinia virus vP410.

The invention is directed to recombinant poxviruses containing therein a DNA sequence from MDV in a nonessential region of the poxvirus genome. The recombinant poxviruses express gene products of the foreign MDV gene. In particular, MDV genes encoding MDV structural proteins were isolated, characterized and inserted into NYVAC (vaccinia virus) and TROVAC (fowlpox virus) recombinants.

Cell Lines and Virus Strains. The strain of FPV designated FP-1 has been previously described (Taylor et al., 1988a,b). It is an attenuated vaccine strain useful in vaccination of day old chickens. The parental virus, Duvette strain, was obtained from Rhone Merieux, Lyon, France. The virus received by Virogenetics was subjected to four successive plaque purifications. One plaque isolate was further amplified in primary CEF cells, and a stock virus, designated as TROVAC, established. TROVAC was deposited under the terms of the Budapest Treaty with the American Type Culture Collection (ATCC), 12301 Parklawn Drive, Rockville, Md., 20852, USA, ATCC accession number VR-2553.

All recombination tests, plaque assays and amplifications with TROVAC or TROVAC based recombinants were performed in primary CEF monolayers made from 10–11 day old embryonated eggs of SPF origin.

The vaccinia virus strain used as a rescue for MDV sequences was NYVAC (vP866). NYVAC is a highly attenuated strain of vaccinia virus derived from the Copenhagen strain by deletion of 18 open reading frames which have been implicated in determining viral virulence and host range restriction. NYVAC was deposited under the terms of the Budapest Treaty with the ATCC, accession number VR-2559. Recombinant plaque selection and virus amplifications were performed on rabbit kidney cells (RK13, ATCC CCL37).

Plasmids pMDV517 and pUC13gB contain DNA sequences encoding MDV gD and gB glycoproteins from strain RB1B. Plasmid pUC13gB contains a 3.9 Kb DNA fragment of genomic DNA of MDV (strain RB1B). The fragment which contains the MDVgB gene is inserted into pUC13 as an EcoRI-SalI fragment. The sequence of the inserted fragment is described in Ross et al. (1989). Plasmid pMDV517 contains a 5.2 Kb DNA fragment of genomic DNA of MDV (strain RB1B). The fragment which contains the MDVgD gene is inserted at the EcoRI site of pUC13. The sequence of the fragment is described in Ross et al. (1991).

Example 1 - ATTENUATED VACCINIA VACCINE STRAIN NYVA

To develop a new vaccinia vaccine strain, the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al. (1990a,b).

The deletion loci were also engineered as recipient loci for the insertion of foreign genes.

The regions sequentially deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7-K1L) vP804; and (6) large subunit, ribonucleotide reductase (I4L) vP866 (NYVAC).

DNA Cloning and Synthesis. Plasmids were constructed, screened and grown by standard procedures (Maniatis et al., 1982; Perkus et al., 1985; Piccini et al., 1987). Restriction endonucleases were obtained from GIBCO/BRL, Gaithersburg, Md.; New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

isolated. This vector fragment was ligated with annealed synthetic oligonucleotides MPSYN45/MPSYN46 (SEQ ID NO:3/SEQ ID NO:4)

|  |  | HindIII SmaI |  |  |
|---|---|---|---|---|
| MPSYN45 | 5' | AGCTTCCCGGGTAAGTAATACGTCAAGGAGAAAACGAA |  |  |
| MPSYN46 | 3' | AGGGCCCATTCATTATGCAGTTCCTCTTTTGCTT |  |  |
|  |  | NotI SspI |  |  |
|  |  | ACGATCTGTAGTTAGCGGCCGCCTAATTAACTAAT | 3' | MPSYN45 |
|  |  | TGCTAGACATCAATCGCCGGCGGATTAATTGATTA | 5' | MPSYN46 |

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, CT) in an automated Perkin Elmer Cetus DNA Thermal Cycler. Excess DNA sequences were deleted from pLasmids by restriction endonuclease digestion followed by limited digestion by BAL-31 exonuclease and mutagenesis (Mandecki 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Panicali et al., 1982; Perkus et al., 1989).

Construction of Plasmid pSD460 for Deletion of Thymidine Kinase Gene (J2R). Referring now to FIG. 1, plasmid pSD406 contains vaccinia HindIII J (pos. 83359–88:377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with Nla:III and a 0.5 kb HindIII/NlaIII fragment isolated. Annealed synthetic oligonucleotides MPSYN43/MPSYN44 (SEQ ID NO:1/SEQ ID NO:2)

|  |  | SmaI |  |
|---|---|---|---|
| MPSYN43 | 5' | TAATTAACTAGCTACCCGGG | 3' |
| MPSYN44 | 3' | GTACATTAATTGATCGATGGGCCCTTAA | 5' |
|  |  | NlaIII EcoRI |  | were ligated with the 0.5 kb HindIII/NlaIII fragment into pUC18 vector plasmid cut with HindIII/EcoRI, generating pasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment generating p SD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. A $^{32}$p labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus; vP410 was identified by plaque hybridization.

Figure 2:
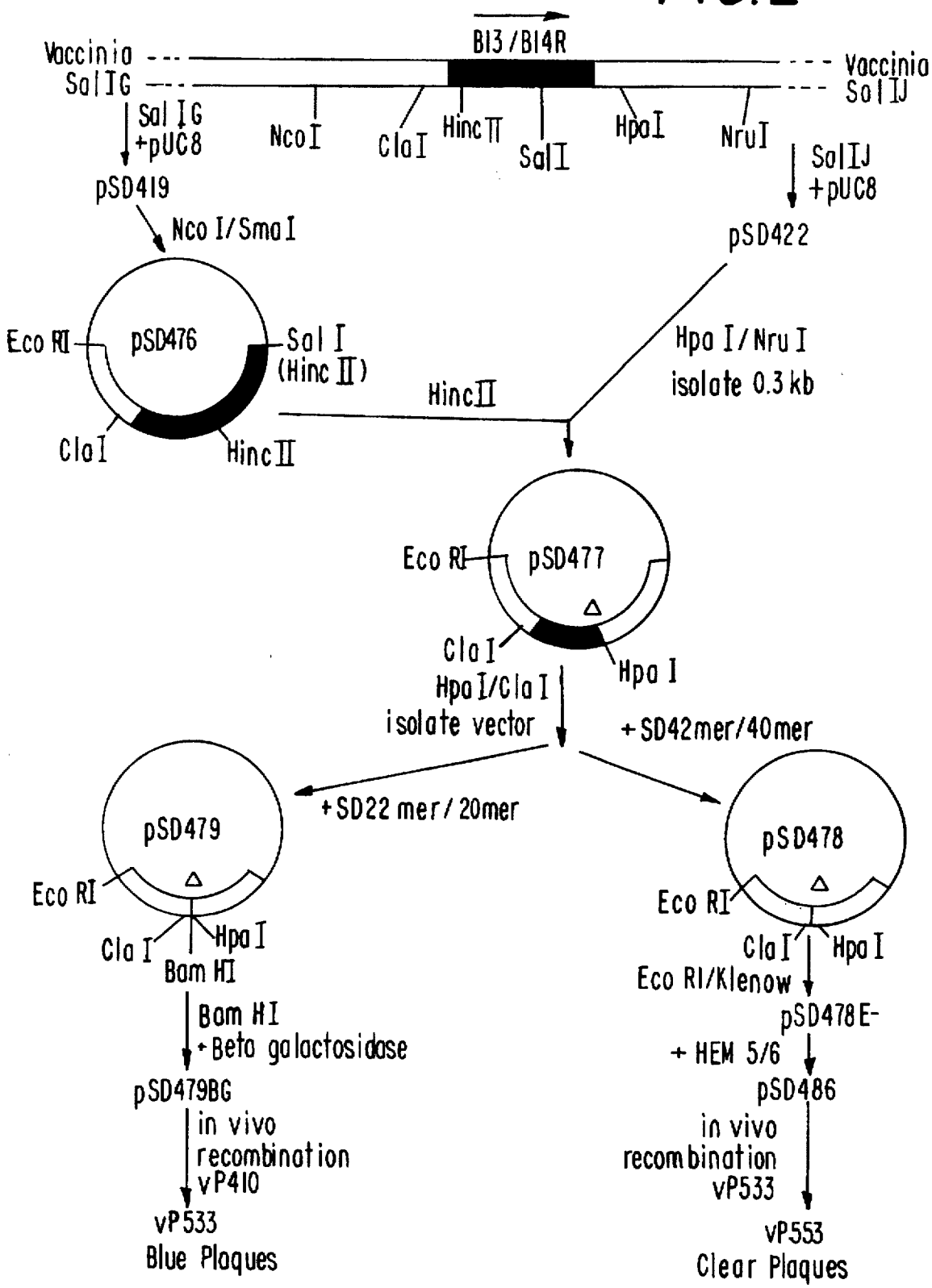
FIG. 2 schematically shows a method for the construction of plasmid pSD486 for deletion of hemorrhagic region and generation of recombinant vaccinia virus vP553.

Construction of Plasmid pSD486 for Deletion of Hemorrhagic Region (B13R+B14R). Referring now to FIG. 2, plasmid pSD419 contains vaccinia SalI G (pos. 160, 744–173,351) cloned into pUC8. pSD422 contains the contiguous vaccinial SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172.253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with (ClaI/HpaI, and the resulting vector fragment was ligated with annealed synthetic oligonucleotides SD22mer/ SD20mer (SEQ ID NO:6/SEQ ID NO:7)

|  |  | ClaI BamHI HpaI |  |
|---|---|---|---|
| SD22mer | 5' | CGATTACTATGAAGGATCCGTT | 3' |
| SD20mer | 3' | TAATGATACTTCCTAGGCAA | 5' | generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
            ClaI          SacI           XhoI        HpaI
SD42mer  5' CGATTACTAGATCTGAGCTCCCCGGGCTCGAGGGATCCGTT  3'
SD40mer  3' TAATGATCTAGACTCGAGGGGCCCGAGCTCCCTAGGCAA    5'
                BglII         SmaI           BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO: 11)

```
           BamHI   EcoRI   HpaI
     HEM5  5'  GATCCGAATTCTAGCT   3'
     HEM6  3'      GCTTAAGATCGA   5'
``` generating plasmid pSD486. pSD486 was used as donor plasmid for recombination with recombinant vaccinia virus vP533, generating vP553, which was isolated as a clear plaque in the presence of X-gal.

Figure 3:
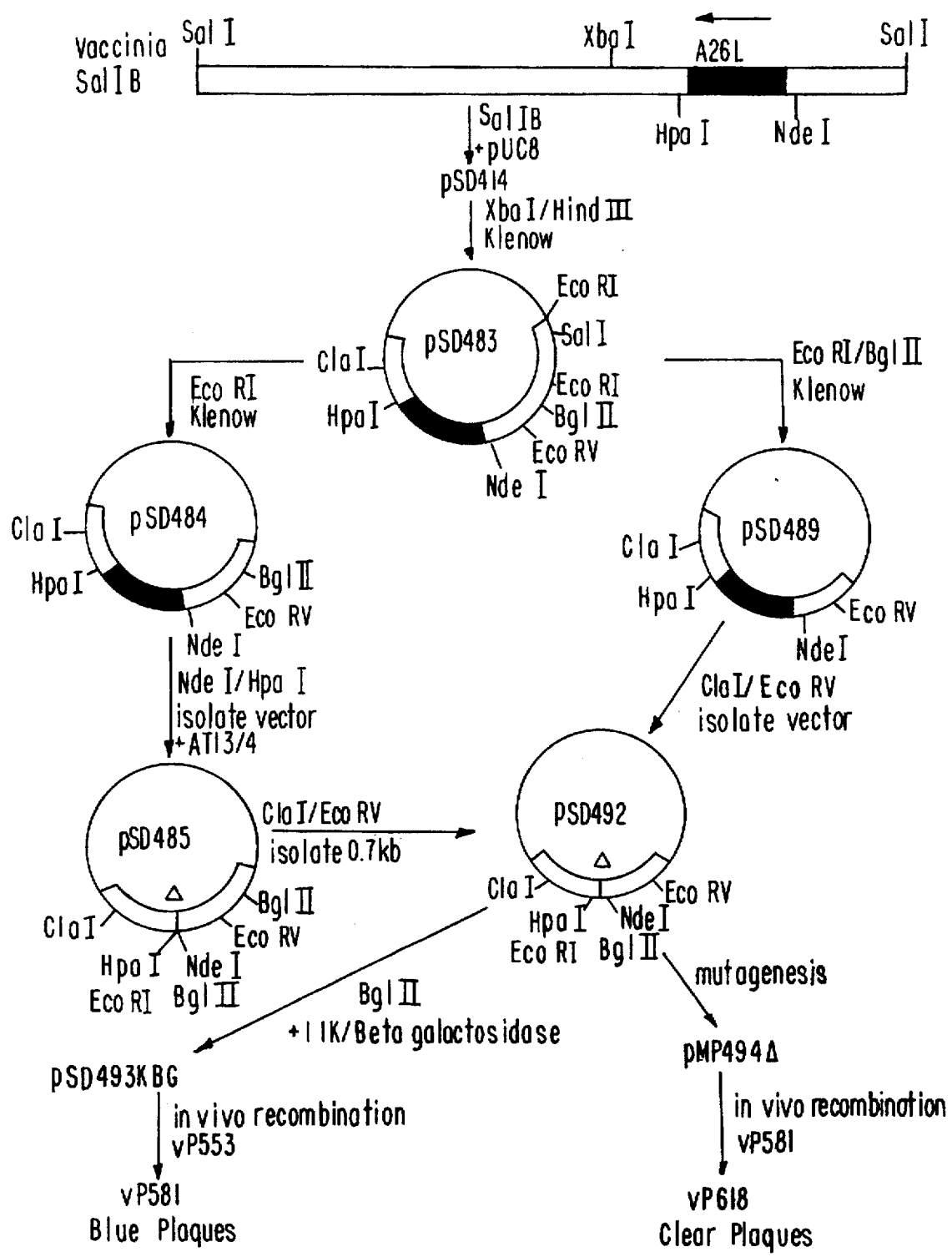
FIG. 3 schematically shows a method for the construction of plasmid pMP494Δ for deletion of ATI region and generation of recombinant vaccinia virus vP618.

Construction of Plasmid pMP494A for Deletion of ATI Region (A26L). Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

from plasmid pSD483 (described above) by digestion with BcfIII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD)492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vF581, the polylinker region of plasmid pSD492 was deleted by mutagenesis (Mandecki, 1986) using synthetic oligonucleotide MPSYN177 (SEQ ID NO:14) (5'AAAATGGGCGTGGATTGTTAACTTTATATAACTT ATTTTTTGAATATAC 3'). In the resulting plasmid, pMP494A, vaccinia DNA encompassing positions [137, 889–138,937], including the entire A26L ORF is deleted. Recombination between the pMP494A and the Beta-galactosidase containing vaccinia recombinant, vP581, resulted in vaccinia deletion mutant vP618, which was isolated as a clear plaque in the presence of X-gal.

Figure 4:
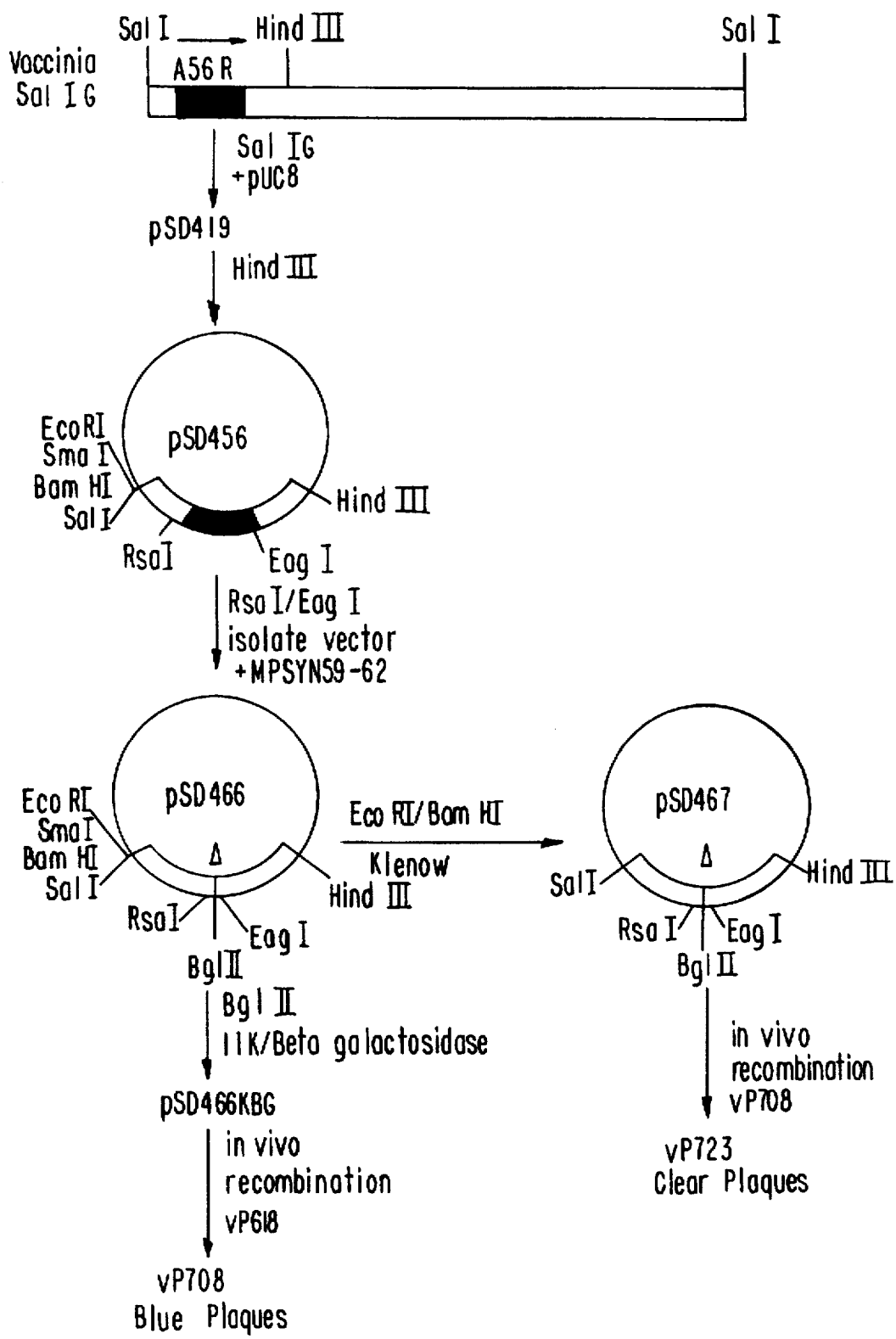
FIG. 4 schematically shows a method for the construction of plasmid pSD467 for deletion of hemagglutinin gene and generation of recombinant vaccinia virus vP723.

Construction of Plasmid PSD467 for Deletion of Hemagglutinin Gene (A56R). Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right.

```
            NdeI
ATI3  5'  TATGAGTAACTTAACTCTTTTGTTAATTAAAAGTATATTCAAAAAATAAGT
ATI4  3'      ACTCATTGAATTGAGAAAACAATTAATTTTCATATAAGTTTTTTATTCA
              BglII  EcoRI  HpaI
      TATATAAATAGATCTGAATTCGTT     3'  ATI3
      ATATATTTATCTAGACTTAAGCAA     5'  ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62

(SEQ ID NO:16), MPSYN60 (SEQ ID NO:17), and MPSYN 61 (SEQ ID NO:18)

```
            RsaI
MPSYN59  5'  ACACGAATGATTTTCTAAAGTATTTGGAAAGTTTTATAGGTAGTTGATAGA-
MPSYN62  3'  TGTGCTTACTAAAAGATTTCATAAACCTTTCAAAATATCCATCAACTATCT      5'
MPSYN59      -ACAAAATACATAATTT 3'
                                                            BglII
MPSYN60  5'                    TGTAAAAATAAATCACTTTTTATACTAAGATCT-
MPSYN61  3'  TGTTTTATGTATTAAAACATTTTTATTTAGTGAAAAATATGATTCTAGA-
             SmaI   PstI  EagI
MPSYN60      -CCCGGGCTGCAGC       3'
MPSYN61      -GGGCCCGACGTCGCCGG  5'
``` reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 4.

A 3.2 kb BqlII/BamHI (partial) cassette containing the *E. coli* Beta-galactosidase gene (Shapira et al., 1983) under the control of the vaccinia 11 kDa promoter (Bertholet et al., 1985; Guo et al., 1989) was inserted into the BqlII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

Figure 5:
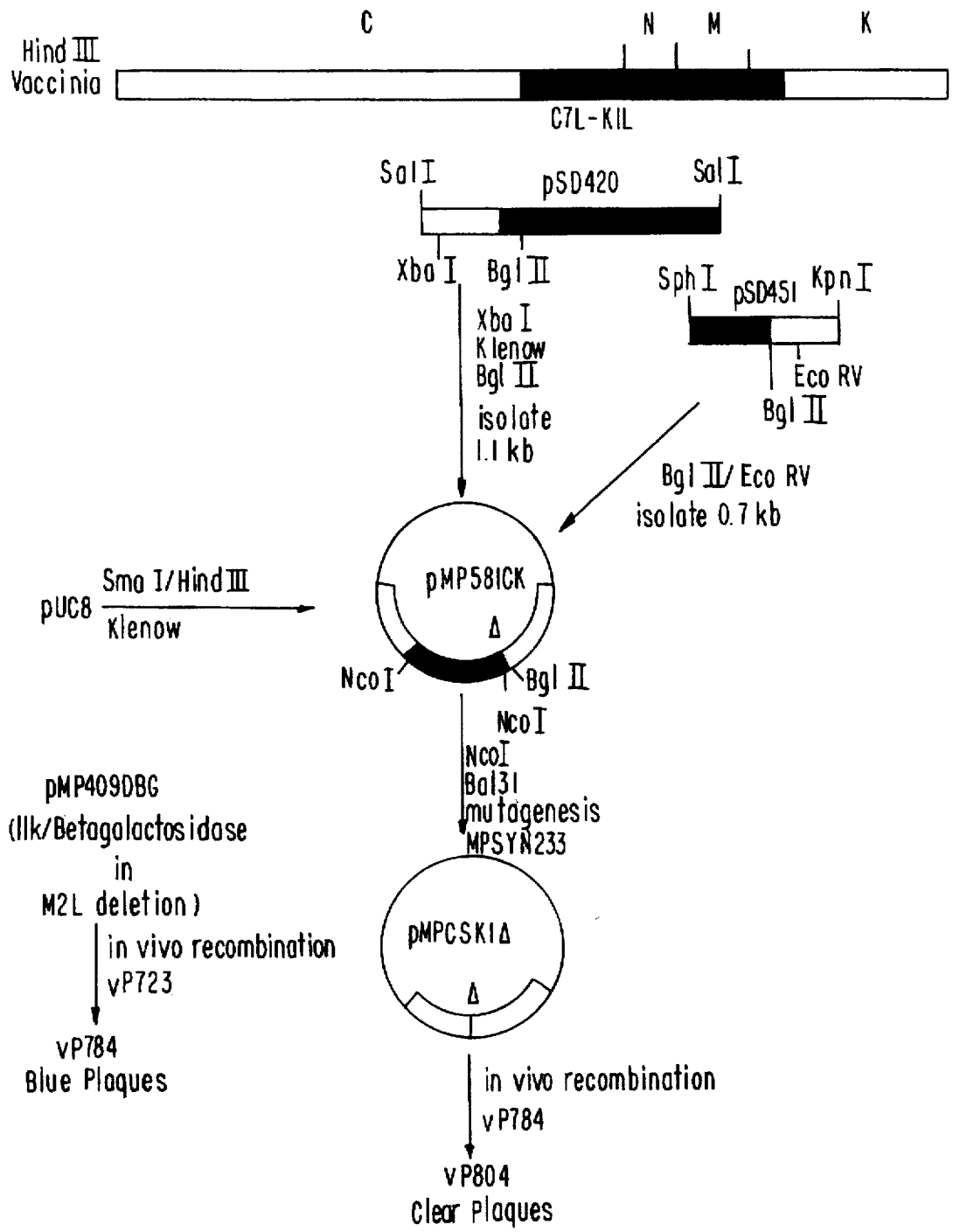
FIG. 5 schematically shows a method for the construction of plasmid pMPCSK1Δ for deletion of gene cluster [C7L-K1L] and generation of recombinant vaccinia virus vP804.

Construction of Plasmid pMPCSK1Δ for Deletion of Open Reading Frames [C7L–K1L]. Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUCS.

To provide a substrate for the deletion of the [C7L–K1L] gene cluster from vaccinia, *E. coli* Beta-galactosidase was first inserted into the vaccinia M2L deletion locus (Guo et al., 1990) as follows. To eliminate the BglII site in pSD409, the plasmid was cut with BqlII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide.

The resulting plasmid, pMP409D, contains a unique BglII site inserted into the M2L deletion locus as indicated above.

A 3.2 kb BamHI (partial)/BglII cassette ontaining the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pucs cut with SmaI, HindIII and blunt ended with Klenow fragment of *E. coli* polymerase. The left flanking arm consisting of vaccinia HindIII C sequences was obtained by digestion of pSD420 w ith XbaI (pos. 18,628) followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the 1985 II site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5' TGTCATTTAACACTATACTCATAT-TAATAAAAATAATATTTATT 3'.

The resulting plasmid, pMPCSK1Δ, is deleted for vaccinia sequences positions 18,805–29,108, encompassing 12 vaccinia open reading frames [C7L –K1L]. Recombination between pMPCSK1A and the Beta-galactosidase containing vaccinia recombinant, vP784, resulted in vaccinia deletion mutant, vP804, which was isolated as a clear plaque in the presence of X-gal.

Figure 6:
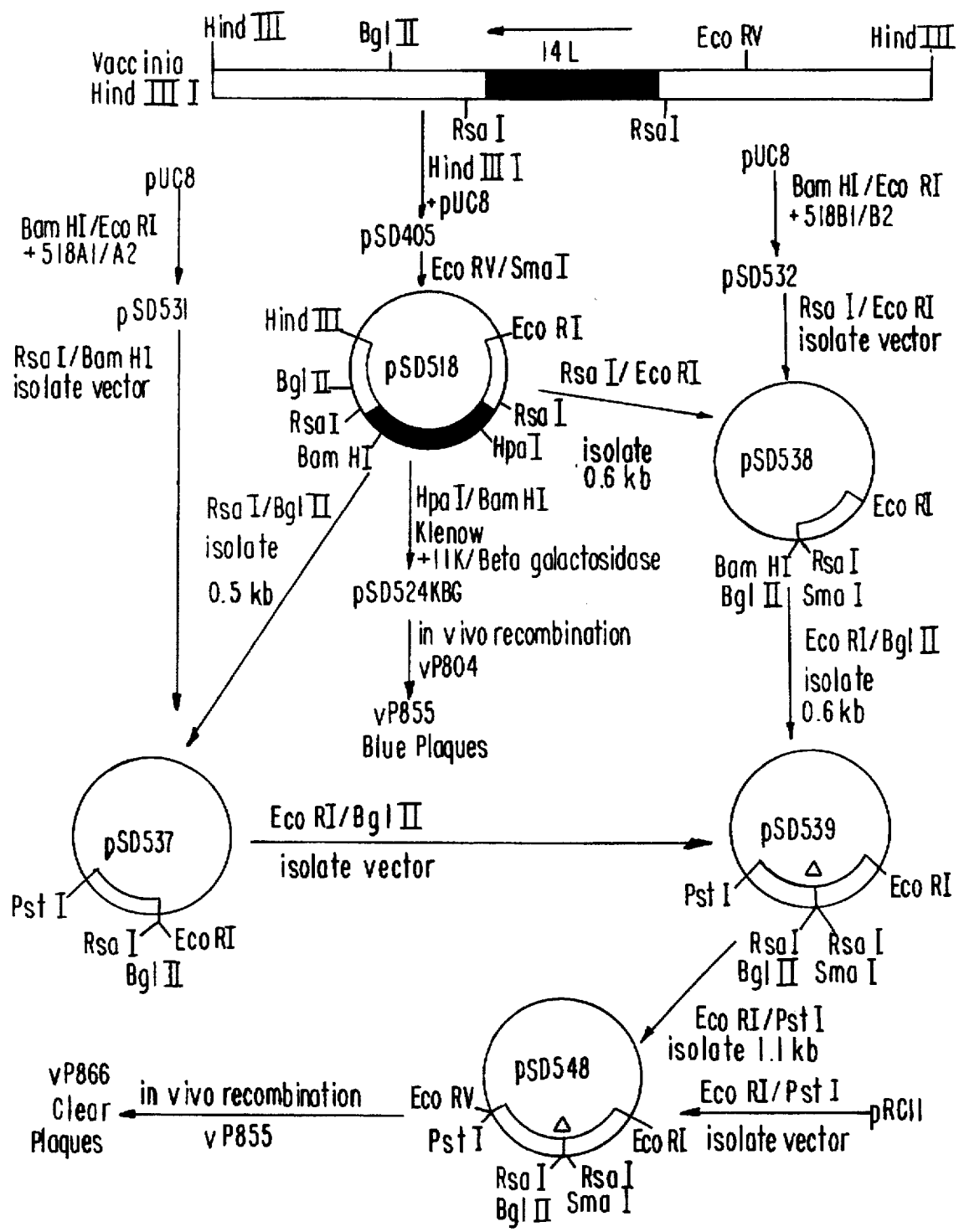
FIG. 6 schematically shows a method for the construction of plasmid pSD548 for deletion of large subunit, ribonucleotide reductase and generation of recombinant vaccinia virus vP866 (NYVAC)

Construction of Plasmid pSD548 for Deletion of Large Subunit, Ribonucleotide Reductase (I4L). Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

```
                                                     BglII
MPSYN82  (SEQ ID NO:19)  5'  TTTCTGTATATTTGCACCAATTTAGATCTTACTCAAAA
                             TATGTAACAATA 3'
```

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BanHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

ing plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected.

```
          BamHI    RsaI
518A1  5' GATCCTGAGTACTTTGTAATATAATGATATATATTTTCACTTTATCTCAT
518A2  3'     GACTCATGAAACATTATATTACTATATATAAAAGTGAAATAGAGTA
                          BglII      EcoRI
          TTGAGAATAAAAAGATCTTAGG         3'  518A1
          AACTCTTATTTTTCTAGAATCCTTAA     5'  518A2
``` forming plasmid pSD531. pSD531 was cut with RsaI (partial) and BamHI and a 2.7 kb vector fragment isolated. pSD518 was cut with BglII (pos. 64,459)/ RsaI (pos. 64,994) and a 0.5 kb, fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vPS66, containing the six engineered deletions as described above, was designated vaccinia vaccine strain "NYVAC."

```
          BamHI      BglII   SmaI
518B1  5' GATCCAGATCTCCCGGGAAAAAAATTATTTAACTTTTCATTAATAGGGATTT
518B2  3'     GTCTAGAGGGCCCTTTTTTTAATAAATTGAAAAGTAATTATCCCTAAA
                    RsaI      EcoRI
          GACGTATGTAGCGTACTAGG          3'  518B1
          CTGCATACTACGCATGATCCTTAA      5'  518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of the I4L coding sequences.

The right vaccinia flanking arm was isolated as ia 0.6 kb EcoRI/BglII fragment from pSD538 and ligated into pSD537 vector plasmid cut with EcoRI/BglII. In the result- Example 2 - PLASMID CONSTRUCTIONS Construction of Fowlpox Insertion Plasmid at F8 Locus. Plasmid pRW731.15 contains a 10 Kbp PvuII-PvuII fragment cloned from TROVAC genomic DNA. The nucleotide sequence was determined on both strands for a 3660 bp PvuII-EcORV fragment. This sequence is as follows (SEQ ID NO:25):

| | | | | | |
|---|---|---|---|---|---|
| 1 GATATCTGTG | GTCTATATAT | ACTACACCCT | ACCGATATTA | ACCAACGAGT | TTCTCACAAG |
| 61 AAAACTTGTT | TAGTAGATAG | AGATTCTTTG | ATTGTGTTTA | AAAGAAGTAC | CAGTAAAAAG |
| 121 TGTGGCATAT | GCATAGAAGA | AATAAACAAA | AAACATATTT | CCGAACAGTA | TTTTGGAATT |

-continued

| | | | | | |
|---|---|---|---|---|---|
| 181 CTCCCAAGTT | GTAAACATAT | TTTTTGCCTA | TCATGTATAA | GACGTTGGGC | AGATACTACC |
| 241 AGAAATACAG | ATACTGAAAA | TACGTGTCCT | GAATGTAGAA | TAGTTTTTCC | TTTCATAATA |
| 301 CCCAGTAGGT | ATTGGATAGA | TAATAAATAT | GATAAAAAAA | TATTATATAA | TAGATATAAG |
| 361 AAAATGATTT | TTACAAAAAT | AACCTATAAG | AACAATAAAA | ATATAATTAC | ATTTACGGAA |
| 421 AATAGCTGGT | TTTAGTTTAC | CAACTTAGAG | TAATTATCAT | ATTGAATCTA | TATTGTTTTT |
| 481 TAGTTATATA | AAAACATGAT | TAGCCCCCAA | TCGGATGAAA | ATATAAAAGA | TGTTGAGAAT |
| 541 TTCGAATACA | ACAAAAAGAG | GAATCGTACG | TTGTCCATAT | CCAAACATAT | AAATAAAAAT |
| 601 TCAAAAGTAG | TATTATACTG | GATGTTTAGA | GATCAACGTG | TACAAGATAA | TTGGGCTTTA |
| 661 ATTTACGCAC | AACGATTAGC | GTTAAAACTC | AAAATACCTC | TAAGAATATG | CTTTTGTGTC |
| 721 GTGCCAAAAT | TTCACACTAC | TACTTCTAGA | CACTTTATGT | TTTTAATATC | CGGTCTTAAA |
| 781 GAAGTCGCGG | AAGAATGTAA | AAGACTATGT | ATAGGGTTTT | CATTGATATA | TGGCGTACCA |
| 841 AAAGTAATAA | TTCCGTGTAT | AGTAAAAAAA | TACAGAGTCG | GAGTAATCAT | AACGGATTTC |
| 901 TTTCCATTAC | GTGTTCCCGA | AAGATTAATG | AAACAGACTG | TAATATCTCT | TCCAGATAAC |
| 961 ATACCTTTTA | TACAAGTAGA | CGCTCATAAT | ATAGTACCTT | GTTGGGAAGC | TTCTGATAAA |
| 1021 GAAGAATACG | GTGCACGAAC | TTTAAGAAAA | AAGATATTTG | ATAAATTATA | TGAATATATG |
| 1081 ACAGAATTTC | CTGTTGTTCG | TAAACATCCA | TACGGTCCAT | TTTCTATATC | TATTGCAAAA |
| 1141 CCCAAAAATA | TATCATTAGA | CAAGACGGTA | TTACCCGTAA | AATGGGCAAC | GCCTGGAACA |
| 1201 AAAGCTGAA | TAATTGTTTT | AAAAGAATTT | ATAAAAAACA | GATTACCGTC | ATACGACGCG |
| 1261 GATCATAACA | ATCCTACGTG | TGACGCTTTG | AGTAACTTAT | CTCCGTGGCT | ACATTTGGT |
| 1321 CATGTATCCG | CACAACGTGT | TGCCTTAGAA | GTATTAAAAT | GTATACGAGA | AAGCAAAAAA |
| 1381 AACGTTGAAA | CGTTTATAGA | TGAAATAATT | GTAAGAAGAG | AACTATCGGA | TAATTTTTGT |
| 1441 TACTATAACA | AACATTATGA | TAGTATCCAG | TCTACTCATT | CATGGGTTAG | AAAAACATTA |
| 1501 GAAGATCACA | TTAATGATCC | TAGAAAGTAT | ATATATTCCA | TTAAACAACT | CGAAAAAGCG |
| 1561 GAAACTCATGA | ATCCTCTATG | GAACGCGTCA | CAAATGCAGA | TGGTGAGAGA | AGGAAAAATG |
| 1621 CATAGTTTTT | TACGAATGTA | TTGGGCTAAG | AAGATACTTG | AATGGACTAG | AACACCTGAA |
| 1681 GACGCTTTGA | GTTATAGTAT | CTATTTGAAC | AACAAGTACG | AACTAGACGG | CACGGATCCT |
| 1741 AACGGATACG | TAGGTTGTAT | GTGGTCTATT | TGCGGATTAC | ACGATAGAGC | GTGGAAAGCA |
| 1801 AGACCGATAT | TTGGAAAGAT | AAGATATATG | AATTATGAGA | GTTCTAAGAA | GAAATTTGAT |
| 1861 GTTGCTGTAT | TTATACAGAA | ATACAATTAA | GATAAATAAT | ATACAGCATT | GTAACCATCG |
| 1921 TCATCCGTTA | TACGGGGAAT | AATATTACCA | TACAGTATTA | TTAAATTTTC | TTACGAAGAA |
| 1981 TATAGATCGG | TATTTATCGT | TAGTTTATTT | TACATTTATT | AATTAAACAT | GTCTACTATT |
| 2041 ACCTGTTATG | GAAATGACAA | ATTTAGTTAT | ATAATTTATG | ATAAAATTAA | GATAATAATA |
| 2101 ATGAAATCAA | ATAATTATGT | AAATGCTACT | AGATTATGTG | AATTACGAGG | AAGAAAGTTT |
| 2161 ACGAACTGGA | AAAAATTAAG | TGAATCTAAA | ATATTAGTCG | ATAATGTAAA | AAAAATAAAT |
| 2221 GATAAAACTA | ACCAGTTAAA | AACGGATATG | ATTATATACG | TTAAGGATAT | TGATCATAAA |
| 2281 GGAAGAGATA | CTTGCGGTTA | CTATGTACAC | CAAGATCTGG | TATCTTCTAT | ATCAAATTGG |
| 2341 ATATCTCCGT | TATTCGCCGT | TAAGGTAAAT | AAAATTATTA | ACTATTATAT | ATGTAATGAA |
| 2401 TATGATATAC | GACTTAGCGA | AATGGAATCT | GATATGACAG | AAGTAATAGA | TGTAGTTGAT |
| 2461 AAATTAGTAG | GAGGATACAA | TGATGAAATA | GCAGAAATAA | TATATTTGTT | TAATAAATTT |
| 2521 ATAGAAAAAT | ATATTGCTAA | CATATCGTTA | TCAACTGAAT | TATCTAGTAT | ATTAAATAAT |
| 2581 TTTATAAATT | TTATAAATTT | TAATAAAAAA | TACAATAACG | ACATAAAGAT | ATTTAATCTT |
| 2641 TAATTCTTGA | TCTGAAAAAC | ACATCTATAA | AACTAGATAA | AAAGTTATTC | GATAAAGATA |
| 2701 ATAATGAATC | GAACGATGAA | AAATTGGAAA | CAGAAGTTGA | TAAGCTAATT | TTTTTCATCT |
| 2761 AAATAGTATT | ATTTTATTGA | AGTACGAAGT | TTTACGTTAG | ATAAATAATA | AAGGTCGATT |
| 2821 TTTACTTTGT | TAAATATCAA | ATATGTCATT | ATCTGATAAA | GATACAAAAA | CACACGGTGA |
| 2881 TTATCAACCA | TCTAACGAAC | AGATATTACA | AAAAATACGT | CGGACTATGG | AAAACGAAGC |
| 2941 TGATAGCCTC | AATAGAAGAA | GCATTAAAGA | AATTGTTGTA | GATGTTATGA | AGAATTGGGA |
| 3001 TCATCCTCAA | CGAAGAAATA | GATAAAGTTC | TAAACTGGAA | AAATGATACA | TTAAACGATT |
| 3061 TAGATCATCT | AAATACAGAT | GATAATATTA | AGGAAATCAT | ACAATGTCTG | ATTAGAGAAT |
| 3121 TTGCGTTTAA | AAAGATCAAT | TCTATTATGT | ATAGTTATGC | TATGGTAAAA | CTCAATTCAG |
| 3181 ATAACGAACA | TTGAAAGATA | AAATTAAGGA | TTATTTTATA | GAAACTATTC | TTAAAGACAA |
| 3241 ACGTGGTTAT | AAACAAAAGC | CATTACCCGG | ATTGGAAACT | AAAATACTAG | ATAGTATTAT |
| 3301 AAGATTTTAA | AAACATAAAA | TTAATAGGTT | TTTATAGATT | GACTTATTAT | ATACAATATG |
| 3361 GATAAAAGAT | ATATATCAAC | TAGAAAGTTG | AATGACGGAT | TCTTAATTTT | ATATTATGAT |
| 3421 TCAATAGAAA | TTATTGTCAT | GTCGTGTAAT | CATTTTATAA | ATATATCAGC | GTTACTAGCT |
| 3481 AAGAAAAACA | AGGACTTTAA | TGAATGGCTA | AAGATAGAAT | CATTTAGAGA | AATAATAGAT |
| 3541 ACTTTAGATA | AAATTAATTA | CGATCTAGGA | CAACGATATT | GTGAAGAACT | TACGGCGCAT |
| 3601 CACATTCCAG | TGTAATTATT | GAGGTCAAAG | CTAGTAACTT | AATAGATGAC | AGGACAGCTG |

The limits of an open reading frame designated as F8 were determined within this sequence. The open reading frame is initiated at position 496 and terminates at position 1887. The engineered deletion was made from position 780 to position 1927, as described below.

Plasmid pRW761 is a sub-clone of pRW731.15 containing a 2429 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:26) and JCA018 (SEQ ID NO:27).

| | |
|---|---|
| JCA017: | CTAGACACTTTATGTTTTTTAATATCCGGTCTTAAAAGCTTCCCGGGGATCCTTA TACGGGGAATAAT 3' |
| JCA018: | ATTATTCCCCGTATAAGGATCCCCCGGGAAGCTTTTAAGACCGGATATTAAAAA CATAAAGTGT 3' |

The plasmid resulting from this ligation was designated pJCA002.

Additional cloning sites were incorporated into pJCA002 by inserting the annealed and kinased oligonucleotides CE205 (SEQ ID NO:28) and CE206 (SEQ ID NO:29) into the BamHI and HindIII sites of pJCA002 to form pCE72.

```
CE205:  GATCAGAAAAACTAGCTAGCTAGTACGTAGTTAACGTCGACCTGCAGAAGCTTCT
        AGCTAGCTAGTTTTTAT
CE206:  AGCTATAAAAACTAGCTAGCTAGAAGCTTCTGCAGGCTCGACGTTAACTACGTAC
        TAGCTAGCTAGTTTTTCT
```

In order to increase the length of the FPV flanking arms in the insertion plasmid, plasmid pJCA021 was constructed. Plasmid pJCA021 was obtained by inserting a 4900bp PvuII-HiLndII fragment from PRW 731.15 (previously described) into the SmaI and HindII sites of pBluescript SS $K^+$ (Stratagene, La Jolla, Calif.). A BglII to EcoRI fragment from pCE72 was then ligated into the BglII and EcoRI sites of pJCA021 to generate pCEN100.

Construction of a Plasmid for Insertion of MDV gB Sequence into TROVAC. Three fragments generated by the Polymerase Chain Reaction (PCR) were necessary for construction of an insertion plasmid. Reaction 1 created a fragment which contained the vaccinia virus H6 promoter fused in a precise ATG:ATG configuration with the 5' end of the MDV gB gene. For this reaction, plasmid pRW825 containing the H6 promoter previously described (Taylor et al., 1988a,b; Guo et al., 1989) was used as a template and oligonucleotides RW297 (SEQ ID NO:30) and RW298 (SEQ ID NO:31) as primers.

```
RW297:  GACCTCGTCGACAATACGACTCACTATAGGGAG
RW298:  GAAGAATATGCAATTCCGCCTAAAATAGTGCATTACGATACAAACTTAA
```

Reaction 2 generated a fragment containing the 5' end of the MDV gB gene in which a TTTTTTT sequence was changed to TATTCTT to eliminate the possibility of early termination (Yuen and Moss, 1987). The 3' end of the fragment generated, overlapped the 5' end of the fragment generated in reaction 3. In reaction 2, plasmid pUC13gB containing the MDV gB coding sequence was used as a template and oligonucleotides RW299 (SEQ ID NO:32) and RW300 (SEQ ID NO:33) as primers.

```
RW299:  ATGCACTATTTTAGGCGGAATTGCATATTCTTCCTTATAGTTATTC
RW300:  ATATCTACGATGATTTTCTAGGTTCGGGACATTTTC
```

Reaction 3 generated a fragment defining the 3' end of the MDV gB gene and removed non-coding sequences contained in pUC13gB. Plasmid pUC13gB was used as a template for this reaction and RW 301 (SEQ ID NO:34) and RW302 (SEQ ID NO:35) as primers.

```
RW301:  GTCCCGAACCTAGAAAATCATCGTAGATATTTTCTG
RW302:  CCTCAGGAATTCGTCGACTATTTACACAGCATCATCTTCTGAG
```

Products of these three PCR reactions were pooled and used as a template for primers RW297 (SEQ ID NO:30) and RW302 (SEQ ID NO:35) in a fourth PCR. The final 1250 bp PCR product was isolated, cut with HincII and inserted into plasmid pCEN100 which had been cut with HincII to derive pRW871. Derivation of plasmid pCEN100 which contains TROVAC genomic DNA directing insertion to the F8 locus is described above. Plasmid pRW371 was partially cut with XbaI, the linear product isolated, recut with AflII and the 7.7 kbp fragment was isolated. Plasmid pUC13gB was digested with AflII and XbaI and the resulting 2140bp fragment containing the gB coding region was inserted into the 7.7 kbp fragment derived from pRW871. The resulting plasmid, pRW878, was used in in vitro recombination with TROVAC as the rescuing virus to derive recombinant vFP108.

Construction of a Plasmid for Insertion of MDV gB into Vaccinia Virus. Plasmid pRW878, previously described, was digested with HincII and the 2.8 kbp fragment containing the MDV gB coding sequence linked to the vaccinia virus H6 promoter was inserted at the SmaI site of vaccinia insertion plasmid pSE)553VC to derive plasmid pRW879. Plasmid pSD553VC is an insertion plasmid utilizing the host range selection system described in Perkus et al. (1989). In this plasmid, the vaccinia virus K1L gene and polylinker regions are located within flanking Copenhagen vaccinia arms, replacing the ATI region (open reading frames A25L and A26L) described in Goebel et al. (1990a,b). The entire region is in a pUC8 vector and insertion sites are flanked by translational stop codons and transcriptional stop signals. Plasmid pRW879 was used in in vitro recombination with NYVAC (vP866) as the rescuing virus to derive recombinant vP935 expressing the Marek's gB gene.

Construction of a Plasmid for Insertion of MDV gD into Vaccinia Virus. Four PCR reactions were used to create an insertion plasmid. In reaction 1, plasmid pRW880 was used as a template to derive a fragment containing the vaccinia virus H6 promoter sequence linked to the MDV gD 5' sequence with the promoter's ATG overlapping the initiating ATG of the MDV gD gene. Plasmid pRW880 contains the previously described H6 promoter sequence linked to a non-pertinent gene in the F16 insertion locus. The primers used in this reaction were RW389 (SEQ ID NO:36) and RW390 (SEQ ID NO:37).

RW389: TGAGATATATCTAAAGAAGAATACTTTCATTACGATACAAACTTAAC
RW390: TAATATAATCTTTTATAC

In the second and third PCR reactions, pMEDV517 was used as a template. Plasmid pMDV517 contains a 5.2 kb DNA fragment containing the MDV gD gene inserted at the EcoRI site of pUC13. The object of the reactions was to change two internal TTTTTNT signals to eliminate the possibility of premature termination (Yuen and Moss, 1987). In reaction two, oligonucleotides RW386 (SEQ ID NO:38) and RW 391 (SEQ ID NO:39) were used as primers to change TTTTTTTTT to TTCTTCTTT.

RW386: CCGTTCAGCTTCTTCGTCAATGGTACAACACGGCTGTTAGAC
RW391: GAGCGGTCGACAAGCTTATAGGCGGGAATATGC

In reaction three, oligonucleotides RW387 (SEQ ID NO:40) and RW388 (SEQ ID NO:41) were used to alter the sequence TTTTTTTGT to CTTCTTCGT.

RW387: TGTTGTACCATTGACGAAGAAGCTGAACGGTTTGCATAGTTTGTTATC
RW388: ATGAAAGTATTCTTCTTTAGATATATCTCATCCAC

The products of the three PCR reactions were pooled and primed with RW390 (SEQ ID NO:37) and RW391 (SEQ ID NO:39) for a fourth PCR reaction. The product of the final PCR reaction was cut with NruI and HindIII, resulting in a 1.2 kbp fragment containing the 31 end of the H6 promoter and the MDV gD coding sequence. Plasmid pRW880 (derivation described below) was digested with NruI and HindIII (which eliminates the non-pertinent gene leaving the 51 end of the H6 promoter), and ligated with the 1.2 kp fragment obtained after digestion of the final PCR product. The resulting plasmid pRW893 was then digested with NotI, releasing a 1.4 kbp fragment containing the H6 promoted MDV gD gene which was inserted into the SmaI site of pSD533VC previously described to generate pRW894. Plasmid pRW894 was used in in vitro recombination with NYVAC (vP861) as the rescuing virus to generate recombinant vP1005 expressing the Marek's gD gene.

Construction of a Fowlpox Insertion Plasmid at the F16 Locus. Plasmid pFP23K-1 contains the 10.5 Kbp HindEII fowlpox DNA fragment described in Tartaglia et al. (1990). Plasmid pFP23K-1 was used as a template for a PCR reaction using the following primers RW264 (SEQ ID NO:42), RW265 (SEQ ID NO:43), RW266 (SEQ ID NO:44) and RW267 (SEQ ID NO:45).

RW264: AATTAACCCGGGATCCAAGCTTCTAGCTAGCTAATTTTT
ATAGCGGCCGCTATAATCGTTAACTTATTAG
RW265: CTAGCTAGAAGCTTGGATCCCGGGTTAATTAATTAATAAAAA
GCGGCCGCGTTAAAGTAGAAAAATG
RW266: GTTACATATGTACAGAATCTGATCATAG
RW267: GCTAGAATTCTCTTAGTTTTTATAGTTG

Primers RW265 and RW266 primed the second reaction. RW266, RW267 and the two products from reactions 1 and 2 were combined for a final PCR. Orientation of the primers on the template is as follows:

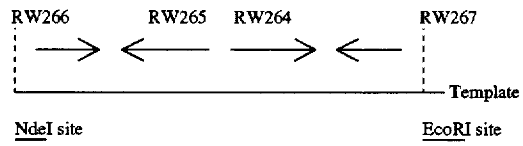

Primer RW266 begins at position 9883 within the 10.5 kbp sequence with an NdeI site. The 5' ends of RW265 and RW264 overlap and are reverse complements. RW265 and RW264 replace the A at position 10054 bp with 61 bp containing the insertion sites SmaI, BamHI and HindIII. Translation termination codons and transcription stop signals flank the insertion sites. The 5' end of RW267 is at position 10229 bp beginning with an EcoRI site.

The third and final PCR product was cut with NdeI and EcoRI and inserted between the NdeI and EcoRI sites of pRW715, resulting in pRW864. Plasmid pRW715 is plasmid pUC9 cut with PvuII and an EcoRI linker was inserted in place of the 300 bp PvuII fragment. In order to insert the *E. coli* LacZ gene plasmid pAMIBG was utilized. Plasmid pAMIBG contains the LacZ BamHI fragment from pMC1871 (Casadaban et al., 1983) inserted in the previously described BamHI site 3 of the 11K vaccintia virus promoter (Paoletti et al., 1984). Plasmid PAMBIG was partially cut with BamHI, the linear product isolated and cut with PstI. The PstI-BamHI fragment containing the 11K promoted LacZ gene was blunt-ended and ligated into the SmaI site of pRW864 (described above). The resulting plasmid was designated pRW867A.

Plasmid PRW866 is a subclone of plasmid pFP23K-1 which contains the 10.5 kbp fowlpox DNA fragment described in Tartaglia et al. (1990). Plasmid pRW866 was constructed by insertion of a 7.3 kpb NaeI to NdeI fowlpox fragment from pFP23K-1 between the PvuII and NdeI sites of pUC9. Plasmid pRW866 contains two FspI sites; one is in pUC and the second at position 1955bp defines the intergenic insertion site designated F16. The FI insertion locus does not interrupt any open reading frame containing an ATG. The linear product of a partial digestion of pRW66 with FsPI was isolated and ligated to a 3.3 kpb NotI fragment from pRW867A containing the 11k promoted LacZ gene. This allowed insertion of the blunt ended LacZ gene fragment into the FspI intergenic insertion site, creating plasmid pRW868. The LacZ gene in pRW868 was then replaced with the 61 bp fragment (previously described) containing SmaI, BamHI and HindIII sites and flanked by transcription termination and translation stop sequences used in development of pRW864. This replacement resulted in plasmid pRW813. Plasmid pRW880 used as a template for the initial construction of plasmid pRW894 contains a non-pertinent gene linked to the H6 promoter in the SmaI site of the F16 insertion locus.

Example 3 - DEVELOPMENT OF POXVIRUS BASED RECOMBINANT EXPRESSING MDV GLYCOPROTEINS Plasmids previously described were transfected into NYVAC or TROVAC infected cells by using the calcium phosphate precipitation method previously described (Panicali and Paoletti, 1982; Piccini et al., 1987). Positive plaques were selected on the basis of hybridization to specific MDV radiolabelled probes and subjected to sequential rounds of plaque purification until a pure population was achieved. Representative plaques from each IVR were then amplified and a stock virus established.

Indirect immunofluorescence was performed as described in Taylor et al. (1990) using a polyclonal chicken anti-MDV serum designated chicken #392.

Immunoprecipitation reactions were performed as described in Taylor et al. (1990) using the reagent described above.

NYVAC Recombinants Expressing MDV Glycoproteins.

Transfection of plasmid pRW879 led to the development of NYVAC recombinant vP935. Immunofluorescence analysis indicated that a protein recognized by MDV immune serum was expressed on the infected cell surface. Immunoprecipitation analysis using the same immune serum from chicken detected the presence of three major expression products with the approximate molecular weights of 110 kDa, 64 kDa and 48 kDa. These sizes correspond to expected products of the MDV gB gene.

Transfection of plasmid pRW894 led to the development of NYVAC recombinant vP1005. A plaque immunoscreen assay indicated that a protein recognized by MDV immune serum was expressed on the infected cell surface. Immunoprecipitation analysis indicated the production of two products with molecular weights of approximately 45 kDa (corresponding to the precursor form of the protein) and 65 kDa which represents the processed glycoprotein.

TROVAC Recombinant Expressing the gB Glycoprotein.

Transfection of plasmid pRW878 led to the development of recombinant vFP108. Immunofluorescence analysis indicated that a protein recognized by MDV immune serum was expressed on the infected cell surface. Immunoprecipitation analysis using the same immune serum from chickens demonstrated the presence of three major expression products with approximate molecular weights of 110 kDa, 64 kDa and 48 kDa.

Example 4 - IMMUNIZATION OF CHICKENS AND SUBSEQUENT CHALLENGE

A group of 25 one day old SPF chickens were inoculated by the subcutaneous route with one dose of 4.0 $\log_{10}$ pfu of TROVAC-MDV gB (vFP108). Ten SPF birds remained uninoculated. At 14 days, the birds including 10 non-vaccinated controls, were challenged by intraperitoneal inoculation of a dilution of the JMV tumor cell line (Nazerian et al., 1977) previously determined to cause 100% mortality, and survivors were assessed.

Results of protection are shown in Table 1.

TABLE 1

| Protective Efficacy of TROVAC-MDV gB (vFP108) in SPF Chickens | | |
|---|---|---|
| Treatment Group | Protection Ratio Survivors/Total | % Survival |
| vFP108* | 11/25 | 44 |
| Non-vaccinated controls | 0/10 | 0 |

*Birds inoculated with 4.0 $\log_{10}$ pfu of vFP108. Birds challenged at 14 days by inoculation with JMV tumor cell line.

In a second experiment, 20 Rhode Island Red Chicks hatched in isolators and free from maternal antibodies to MDV, herpesvirus of turkeys (HVT) and other avian pathogens were vaccinated intramuscularly at one day of age with 6.3 $\log_{10}$ pfu of fowlpox recombinant vFP108. Seven days later the chicks were challenged with MDV by contact infection. This was achieved by mixing the vaccinated chicks with 8 chickens inoculated 15 days previously with 3.0 $\log_{10}$ pfu of the RB1-B strain of MDV. A second group of 20 unvaccinated chicks derived from the same hatch served as controls. These were also challenged with MDV by contact as above. The two groups were kept in separate cages in a high security containment room. A third group of 20 unvaccinated chicks were challenged by inoculation with 3.0$\log_{10}$ pfu of RB1-B and kept in a separate room. This group was included in the experiment to compare the efficiency of challenge by the two methods.

The chicks were observed daily and those that died were examined for gross Marek's disease lesions in visceral organs and peripheral nerves. Tissue samples were taken for histological examination in cases where gross Marek's disease lesions were not obvious.

Two chicks in the group vaccinated with fowlpox recombinant showed symptoms of eye infection, probably due to fowlpox, and died within 2 days after contact with MDV-infected chicks. They were eliminated from the experiment and do not appear in the mortality results shown in Table 2 and FIG. 7.

The results show that vaccination with the fowlpox recombinant delayed mortality significantly. The mean time to death in the vaccinated and unvaccinated group (contact challenge) was 56 days and 35 days respectively. The difference was significant (P<0.005) as shown by analysis of the log transformation of the data using Student's t test.

The total mortality in the two groups after a prolonged period of 19 weeks did not differ significantly as shown by a Chi-square test. However at 6 to 7 weeks post-vaccination, mortality rates differed significantly being almost 100% in the controls and 10% in the vaccinated birds. It should be noted that Broiler chickens are normally sent to market at 6 to 7 weeks of age.

It is clear from FIG. 7 that the challenge by contact infection was efficient compared to challenge by inoculation. The total mortality in the two groups was similar and the slopes of the cumulative mortality curves were also similar after a delay of about 2 weeks (contact infection), which probably represented the time required to establish infection.

It should be noted that the vaccinated group was continuously exposed to MDV shed by the unvaccinated group which was kept in the same room.

In conclusion, the importance of MDV gB as a protective immunogen has been demonstrated under rigorous conditions which involved the use of genetically susceptible chickens vaccinated at one day old, and challenged with MDV by two different methods.

TABLE 2

| | Time to death (days) | |
|---|---|---|
| Fowlpox vaccinated contact challenge | Unvaccinated contact challenge | Unvaccinated inoc. challenge |
| 46 | 36 | 10 |
| 44 | 17 | 26 |
| 110 | 32 | 39 |
| 77 | 48 | 26 |
| 97 | 64 | 42 |
| 53 | 47 | 28 |
| 41 | 31 | 32 |
| 35 | 45 | 24 |
| 56 | 33 | 24 |
| 52 | 32 | 33 |
| 57 | 13 | 10 |
| 51 | 33 | 34 |
| | 48 | 22 |
| | 50 | 10 |
| | 27 | 42 |
| | 45 | 9 |
| | 35 | 29 |
| | 40 | 24 |
| | 38 | |
| Number 12 | 19 | 18 |
| Mean 56 | 35 | 25.7 |
| Total chicks per group 18 | 20 | 19 |

The results indicate the potential of TROVAC-MDV recombinants for vaccination against MDV in the poultry industry. The restricted host range of fowlpox virus provides an inherent safety barrier to transmission of recombinant to non-avian species. Use of antigenic regions of MDV rather than the whole virus eliminates the need to introduce live herpes virus into the environment. The ability of TROVAC to incorporate large amounts of foreign genetic information should allow for inclusion of multiple antigenic determinants from a range of serotypes.

Example 5 - COMPARATIVE EFFICACY OF TROVAC-MDV (vFP108 and HVT)

In previous experiments, the ability of TRQVAC-MDV (vFP108) to protect against MDV challenge was assessed in two ways. In the first experiment, day of age SPF chickens were vaccinated with 40 $\log_{10}$ pfu of vFP108 by the subcutaneous route in the nape of the neck. When birds were challenged at 14 days by intrperitoneal inoculation of the JMV tumor cell line, 44% of birds survived challenge. In the second experiment, day old SPF birds were vaccinated by intramuscular inoculation of 6.3 $\log_{10}$ pfu of vFP108. Seven days later, vaccinated and unvaccinated birds were challenged by contact infection with birds infected with MDV strain RB18. Ninety percent of vaccinated birds Lad survived challenge at 6–7 weeks post-vaccination.

The most commonly used MDV vaccines are the Turkey herpes virus (HVT) vaccines which are seriologically related to MDV. This Example shows the comparative efficacy of HVT and TROVAC-MDV (vFP108).

Twenty day old SPF birds were inoculated with 3.8 $\log_{10}$ $EID_{50}$ of TROVAC-MDV (vFP108) by the subcutaneous route in the nape of the neck. Twenty chicks were inoculated with 3.0 logio pfu of a cell associated HVT vaccine by the subcutaneous route. Ten birds remained uninoculated. Five days post-inoculation, vaccinates and controls were challenged by intraperitoneal inoculation of the RBIB challenge virus. Birds were observed for 49 days at which time they were necropsied and examined for lesions typical of Marek's disease. The results of challenge are shown in Table 3.

The results indicate that 90% of non-vaccinated challenge controls succumbed to infection. Birds vaccinated with TROVAC-MDV (vFP108) showed a 75% survival rate while birds vaccinated with the HVT vaccine showed an 85% survival rate. The result indicates that protection afforded by the TROVAC-MDV (vFP108) vaccine was comparable to the cell associated HVT. Thus, TROVAC-MDV is an effective vaccine.

TABLE 3

Comparative efficacy of TROVAC-MDV (vFP108) and HVT

| Vaccine | Protection Ratio* | % Protection |
|---|---|---|
| TROVAC-MDV (vFP108) | 15/20 | 75 |
| HVT | 17/20 | 85 |
| None | 1/10 | 10 |

*Ratio of birds protected to total number challenged

REFERENCES

1. Bertholet, C., R. Drillien, and R. Wittek, Proc. Natl. Acad. Sci. USA 82, 2096–2100 (1985).
2. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300 (1990a)
3. Boursnell, M. E. G., P. F. Green, J. I. A. Campbell, A. Deuter, R. W. Peters, F. M. Tomley, A. C. R. Samson, P. Chambers, P. T. Emmerson, and M. M. Binns, J. Gen. Virol. 71, 621–628 (1990b).
4. Calnek, B. W. and R. L. Witter. In Diseases of Poultry 9th Edition, eds. B. W. Calnek, H. J. Barnes, C. W. Beard, W. M. Reid and H. W. Yoder, Jr. (Iowa State University Press, Ames, Iowa, USA) pp. 342–385 (1991).
5. Calnek, B. W., K. A. Schat, L. J. N. Ross, W. R. Shek, and C. L. H. Chen, Int. J. Cancer 33, 389–398 (1984).
6. Calnek, B. W., K. A. Schat, E. D. Heller, and C. Buscaglia, In Proc Int Symp Marek's Dis, ed. B. W. Calnek and J. L. Spencer (Am. Assoc. Avian Pathol, Kennett Square, Pa.) pp. 173–187 (1985).
7. Cantin, E. M., R. Eberle, J. L. Baldick, B. Moss, D. E. Willey, A. L. Notkins and H. Openshaw, Proc. Nat. Acad. Sci USA 84, 5908–5912 (1987).
8. Casadaban, M. J., A. Martinez-Arias, S. K. Shapira, and J. Chow, Methods in Enzymology 100, 293–308 (1983).
9. Clewell, D. B., and D. R. Helinski, Proc. Natl. Acad. Sci. USA 62, 1159–1166 (1969).
10. Clewell, D. B., J. Bacteriol. 110, 667–676 (1972).
11. Colinas, R. J., R. C. Condit, and E. Paoletti, Virus; Research 18, 49–70 (1990).
12. Cremer, K. J., M. Mackett, C. Wohlenberg, A. L. Notkins and B. Moss, Science 228, 737–740 (1985).

13. Edbauer, C., R. Weinberg, J. Taylor, A. Rey-Senelonge, J. F. Bouquet, P. Desmettre, and E. Paoletti, Virology 179, 901–904 (1990).
14. Engelke, D. R., P. A. Hoener, and F. S. Collins, Proc. Natl. Acad. Sci. USA 85, 544–548 (1988).
15. Esposito, J. J., Fifth Report of the International Committee on Taxonomy of Viruses, Archives of Virology Supplement 2, eds. R. I. B. Francki, C. M. Faquet, D. L. Knudson, F. Brown, (Springer-Verlag, New York) pp 91–102 (1991).
16. Goebel, S. J., G. P. Johnson, M. E. Perkus, S. W. Davis, J. P. Winslow, and E. Paoletti, Virology 179, 247–266 (1990a).
17. Goebel, S. J., G. P. Johnson, M. E. Perkus, S. W. Davis, J. P. Winslow, and E. Paoletti, Virology 179, 517–563 (1990b).
18. Guo, P., S. Goebel, M. E. Perkus, J. Taylor, E. Norton, G. Allen, B. Languet, P. Desmettre, and E. Paoletti, J. Virol. 64, 2399–2406 (1990).
19. Guo, P., S. Goebel, S. Davis, M. E. Perkus, B. Languet, P. Desmettre, G. Allen, and E. Paoletti, J. Virol. 63, 4189–4198 (1989).
20. Kato, S. and K. Hirai, Adv. Virus Res. 30, 225–277 (1985).
21. Mandecki, W., Proc. Natl. Acad. Sci. USA 83, 7177–7181 (1986).
22. Maniatis, T., E. F. Fritsch, and J. Sambrook, Molecular Cloning, Cold Spring Harbor Laboratory, N.Y. 545 pages (1982).
23. Maniatis, T., E. F. Fritsch, and J. Sambrook, Molecular Cloning, Cold Spring Harbor Laboratory, N.Y. 545 pages (1986).
24. Marchioli, C. C., R. J. Yancey, E. A. Petrovskis, J. G. Timmins and L. E. Post, J. Virol. 61, 3977–3981 (1987).
25. Nazerian, K., E. A. Stephens, J. M. Sharma, L. F. Lee, M. Gailitis and R. L. Witter, Avian Diseases 21, 69–76 (1977).
26. Okazaki, W., H. G. Purchase, B. R. Burmester, Avian Dis 14, 413–429 (1970).
27. Ono, K., M. Takashima, T. Ishikawa, M. Hayashi, I. Yoshida, T. Konobe, K. Ikuta, K. Nakajima, S. Ueda, S. Kato and K. Hirai, Avian Dis 29, 533–539 (1985).
28. Panicali, D., and E. Paoletti, Proc. Natl. Acad. Sci. USA 79, 4927–4931 (1982).
29. Paoletti, E., B. L. Lipinskas, C. Samsonoff, S. Mercer and D. Panicali, Proc. Nat. Acad. Sci. 81, 193–197 (1984).
30. Payne, L.N., J. A. Frazier, P. C. Powell, Int. Rev. Exp. Pathol. 16, 59–153 (1976).
31. Payne, L. N. In Marek's Disease, ed. L. N. Payne (Martinum; Nijhoff, Boston) pp. 43–76 (1985).
32. Perkus, M.E., S.J. Goebel, S.W. Davis, G. P. Johnson, K. Limbach, E. K. Norton, and E. Paoletti, Virology 179, 276–286 (1990).
33. Perkus, M. E., K. Limbach, and E. Paoletti, J. Virol. 63, 3829–3836 (1989).
34. Perkus, M. E., A. Piccini, B. R. Lipinskas, and E. Paoletti, Science 229, 981–984 (1985).
35. Piccini, A., M. E. Perkus, and E. Paoletti, In Methods in Enzymology, Vol. 153, eds. Wu, R., and Grossman, L., (Academic Press) pp. 545–563 (1987).
36. Ross, L. J. N., M. Sanderson, S. D. Scott, M. M. Binns, T. Doel and B. Milne, J. Gen. Virol. 70, 1789–1804 (1989).
37. Ross, L. J. N. and M. M. Binns, J. Gen. Virol. 72, 939–947 (1991).
38. Ross, L. J. N., M. M. Binns and J. Pastorek, J. Gen. Virol. 72, 949–954 (1991).
39. Sanger, F., S. Nicklen, and A. R. Coulson, Proc. Natl. Acad. Sci. USA 74, 5463–5467 (1977).
40. Schat, K. A., Cancer Surveys 6, 1–37 (1987).
41. Shapira, S. K., J. Chou, F. V. Richaud, and M. J. Casadaban, Gene 25, 71–82 (1983).
42. Tabor, S., and C. C. Richardson, Proc. Natl. Acad. Sci. USA 84, 4767–4771 (1987).
43. Tartaglia, J., S. Pincus and E. Paoletti, Crit. Revs. in Immunol. 10, 13–30 (1990).
44. Taylor, J., R. Weinberg, Y. Kawaoka, R. G. Webster, and E. Paoletti, Vaccine 6, 504–508 (1988a).
45. Taylor, J., R. Weinberg, B. Languet, P. Desmettre, and E. Paoletti, Vaccine 6, 497–503 (1988b).
46. Taylor, J., C. Edbauer, A. Rey-Senelonge, J.F. Bouquet, E. Norton, S. Goebel, P. Desmettre, and E. Paoletti, J. Virol. 64, 1441–1450 (1990).
47. Taylor, J., S. Pincus, J. Tartaglia, C. Richardson, G. Alkhatib, D. Briedis, M. Appel, E. Norton, and E. Paoletti, J. Virol. 65, 4263–4272 (1991).
48. Yuen, L., and B. Moss, Proc. Natl. Acad. Sci. USA 84, 6417–6421 (1987).

---

What is claimed is:

1. A recombinant TROVAC fowlpox comprising exogenous DNA encoding at least one of Marek's Disease Virus gB and gD glycoproteins.

2. The recombinant TROVAC fowlpox virus of claim 1 comprising exogenous DNA encoding Marek's Disease Virus gB glycoprotein.

3. The recombinant TROVAC fowlpox virus of claim 1 comprising exogenous DNA encoding Marek's Disease Virus gD glycoprotein.

4. The recombinant TROVAC fowlpox virus of claim 1 comprising exogenous DNA encoding Marek's Disease Virus gB and gD glycoproteins.

5. The recombinant TROVAC fowlpox virus of claim 1 comprising vFP108.

6. An immunological composition comprising a carrier and a recombinant TROVAC fowlpox virus as claimed in any one of claims 1 to 5.

7. The immunological composition of claim 6 which induces a protective immune response and is thus a vaccine.

8. A method for inducing an immunological response in a host comprising administering a recombinant TROVAC fowlpox virus as claimed in any one of claims 1 to 5.

9. A method for inducing an immunological response in a host comprising administering an immunological composition as claimed in claims 6.

10. A method for inducing an immunological response in a host comprising administering an immunological composition as claimed in claims 7.

11. The method of claim 8 wherein the host is a chicken.

12. The method of claim 9 wherein the host is a chicken.

13. The method of claim 10 wherein the host is a chicken.

14. A method for expressing a gene product in vitro comprising contacting cells with a recombinant TROVAC fowlpox virus as claimed in any one of claims 1 to 5.

* * * * *